(12) United States Patent
Hoener et al.

(10) Patent No.: US 10,155,741 B2
(45) Date of Patent: *Dec. 18, 2018

(54) PYRIDINE OR PYRIMIDINE DERIVATIVES

(71) Applicant: Hoffmann-La Roche Inc., Little Falls, NJ (US)

(72) Inventors: Marius Hoener, Basel (CH); Juergen Wichmann, Basel (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/954,964

(22) Filed: Apr. 17, 2018

(65) Prior Publication Data

US 2018/0258066 A1 Sep. 13, 2018

Related U.S. Application Data

(63) Continuation of application No. PCT/EP2016/075590, filed on Oct. 25, 2016.

(30) Foreign Application Priority Data

Oct. 28, 2015 (EP) .................................... 15191887

(51) Int. Cl.
| | | |
|---|---|---|
| *C07D 401/04* | (2006.01) | |
| *C07D 401/14* | (2006.01) | |
| *C07D 239/24* | (2006.01) | |
| *C07D 211/80* | (2006.01) | |
| *A61K 31/444* | (2006.01) | |
| *A61K 31/506* | (2006.01) | |
| *A61P 25/18* | (2006.01) | |

(52) U.S. Cl.
CPC .......... *C07D 401/04* (2013.01); *A61K 31/444* (2013.01); *A61K 31/506* (2013.01); *A61P 25/18* (2018.01); *C07D 211/80* (2013.01); *C07D 239/24* (2013.01); *C07D 401/14* (2013.01)

(58) Field of Classification Search
CPC .. C07D 239/24; C07D 211/80; C07D 333/20; C07D 239/04; A61K 31/4427; A61K 31/505; A61P 25/18
USPC .......... 544/333; 546/257; 514/256, 333, 332
See application file for complete search history.

(56) References Cited

U.S. PATENT DOCUMENTS 10,005,736 B1 * 6/2018 Hoener ................ C07D 403/10

FOREIGN PATENT DOCUMENTS

| WO | 2009/043780 A1 | 4/2009 |
| WO | 2010/051188 A1 | 5/2010 |
| WO | 2016/169902 A1 | 10/2016 |

OTHER PUBLICATIONS

Andersen J Jensen et al., "Excitatory amino acid transporters: recent insights into molecular mechanisms, novel modes of modulation and new therapeutic possibilities" Current Opinion in Pharmacology 20:116-123 (Feb. 1, 2015).
ISR of PCT/EP2016/075590 (dated Jan. 27, 2017).

* cited by examiner

*Primary Examiner* — Venkataraman Balasubramanian
(74) *Attorney, Agent, or Firm* — Mark D. Kafka; Genentech, Inc.

(57) ABSTRACT

The present invention relates to compounds of formula I

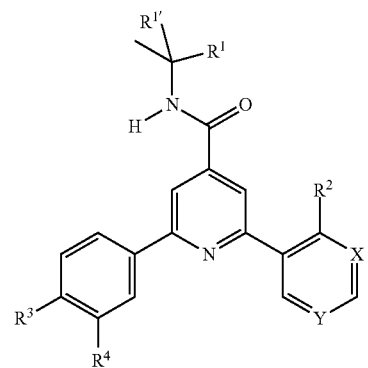

wherein
$R^{1'}$ is methyl;
$R^1$ is methyl, ethyl, $CF_3$, $CH_2OH$, cyclopropyl or cyano, or $R^{1'}$ and $R^1$ may form together a 1,1-dioxo-tetrahydro-thiophen-3-yl ring;
$R^2$ is hydrogen, methyl, ethyl, isopropyl, tert-butyl, cyclopropyl, cyclopropylmethyl, or hydroxymethyl;
$R^3$ is Cl, F, $CF_3$, methyl, methoxy, or cyclopropyl;
$R^4$ is hydrogen, methyl, F or Cl;
X is N or CH;
Y is N or CH;
with the proviso that X and Y are not simultaneously CH; or to a pharmaceutically acceptable salt or acid addition salt, to a racemic mixture, or to its corresponding enantiomer and/or optical isomer and/or stereoisomer.
The compounds of formula I may be used in the treatment of psychiatric disorders such as schizophrenia, bipolar disorder, obsessive-compulsive disorder or autism spectrum disorder.

8 Claims, No Drawings

PYRIDINE OR PYRIMIDINE DERIVATIVES

CROSS-REFERENCE TO RELATED APPLICATIONS

This application is a continuation of, and claims priority to, International Patent Application No. PCT/EP2016/075590, filed on Oct. 25, 2016. This application also claims priority to European Patent Application No. 15191887.7, filed on Oct. 28, 2015. The entire contents of each of the above patent applications are hereby incorporated by reference.

The present invention relates to compounds of formula I

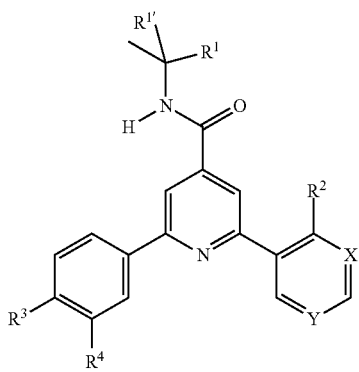

wherein
$R^{1'}$ is methyl;
$R^1$ is methyl, ethyl, $CF_3$, $CH_2OH$, cyclopropyl or cyano, or $R^{1'}$ and $R^1$ may form together a 1,1-dioxo-tetrahydro-thiophen-3-yl ring;
$R^2$ is hydrogen, methyl, ethyl, isopropyl, tert-butyl, cyclopropyl, cyclopropylmethyl, or hydroxmethyl;
$R^3$ is Cl, F, $CF_3$, methyl, methoxy, or cyclopropyl;
$R^4$ is hydrogen, methyl, F or Cl;
X is N or CH;
Y is N or CH;
with the proviso that X and Y are not simultaneously CH; or to a pharmaceutically acceptable salt or acid addition salt, to a racemic mixture, or to its corresponding enantiomer and/or optical isomer and/or stereoisomer.

The compounds of formula I may be used in the treatment of psychiatric disorders such as schizophrenia, bipolar disorder, obsessive-compulsive disorder or autism spectrum disorder.

It has been surprisingly been found that the compounds of general formula I are EAAT3 inhibitors.

The excitatory amino acid transporter 3 (EAAT3), also referred to in human studies as solute carrier family 1, member 1 (systematic gene name: SLC1A1) and in rodents as excitatory amino acid carrier 1 (EAAC1), is a high-affinity anionic amino acid transporter found in neurons throughout the cortex and in the hippocampus, basal ganglia (striatum, thalamus), and the olfactory bulb. EAAT3 functions to buffer local glutamate concentrations at excitatory synapses, for example in the hippocampus, and modulates the differential recruitment of glutamate receptor subtypes at extrasynaptic sites. Furthermore, EAAT3 is thought to be involved in facilitating GABA and glutathione biosynthesis. EAAT3 is a member of the EAAT family that mediates the uptake of glutamate into neuronal and glial cells of the mammalian CNS. Two transporters expressed primarily in glia, EAAT1 and EAAT2, are crucial for glutamate homeostasis in the adult mammalian brain and for rapid clearance of glutamate from the synaptic cleft. Three neuronal transporters (EAAT3, EAAT4, and EAAT5) appear to have additional functions in regulating and processing cellular excitability with EAAT3 being abundantly expressed throughout the CNS (EAAT4 is unique to Purkinje cells of the cerebellum and EAAT5 is expressed in rod photoreceptor and bipolar cells of the retina).

EAATs are assembled as trimers, and the existence of multiple isoforms raises the question of whether certain isoforms can form hetero-oligomers. In the mammalian brain, the specificity of excitatory synaptic transmission depends on rapid diffusion of glutamate away from active synapses and the powerful uptake capacity of glutamate transporters in astrocytes. The extent to which neuronal glutamate transporters influence the lifetime of glutamate in the extracellular space remains unclear, but it is thought to be minor. EAAT3, the predominant neuronal glutamate transporter at excitatory synapses in hippocampal area CA1, buffers glutamate released during synaptic events and prolongs the time course of its clearance by astrocytes. EAAT3 does not significantly alter activation of receptors in the synaptic cleft. Instead, it reduces recruitment of perisynaptic/extrasynaptic NR2B-containing NMDARs, thereby facilitating induction of long-term potentiation by short bursts of high-frequency stimulation. Specific EAAT3 inhibitors may have the potential to locally and specifically strengthen particular synapses.

Obsessive-compulsive disorder (OCD) is among the most common mental disorders (prevalence 1-3%), and is at least as prevalent as schizophrenia and bipolar disorder. In the United States, one in 50 adults suffers from OCD. OCD affects children and adolescents as well as adults. Roughly one third to one half of adults with OCD reports a childhood onset of the disorder, and the disorder is typically chronic in nature. Treatment consists of predominantly serotonergic TCAs (clomipramine) or SSRIs in combination with cognitive-behavioral therapy (CBT). Overall, response to these interventions is of some but still limited benefit (approximately comparable to antidepressant response in MDD), and given the chronicity of OCD, the unmet medical need remains very high. OCD has been linked to serotonin and glutamate abnormalities. The hypothesis of glutamate signaling dysfunction in OCD is based on findings from neuroimaging, animal models, positional cloning and treatment studies.

The obsessive-compulsive symptomatology in OCD has considerable phenomenological, epidemiological and possibly (aetio)-pathophysiological overlap with a core autism spectrum disorder criterion: "restricted, repetitive patterns of behavior, interests, or activities" (taken from proposed DSM-5 revision). In support of this notion, human genetics studies have linked both the serotonin transporter and EAAT3 (SLC1A1) genes to autism spectrum disorder (ASD) or rigid-compulsive behavior in ASD and to OCD.

In addition, obsessive-compulsive symptoms induced by antipsychotics in schizophrenic bipolar disorder patients have been linked to EAAT3 (SLC1A1) gene variants. Postmortem brain studies have shown that both classic and atypical antipsychotics reduce EAAT3, suggesting an involvement of this transporter in neuroleptic mechanisms beyond dopamine and serotonin modulation. Moreover, genetic variation in the human gene EAAT3 (SLC1A1) has been associated with antipsychotic drug response.

There is converging evidence from neurobiological data, human genetics, imaging studies and experimental treatments that EAAT3 is a key pathophysiological element in OCD and rigid-compulsive behavior in autism and in schizophrenia.

Curr. Opin. Pharmacol. 20, 116-123, 2015
J. Neurosci., 32, 2552-2563, 2012

J. Neurosci 29, 14581-14595, 2009
Arch. Gen. Psychiatry, 66, 408-416, 2009
Pharmacol. Ther. 107, 271-285, 2005
J. Neurochem. 98, 1007-1018, 2006
Nat. Neurosci., 9, 119-126, 2006

Compounds of formula I are distinguished by having valuable therapeutic properties. They can be used in the treatment or prevention of disorders, relating to EAAT3 inhibitors.

The most preferred indications for compounds which are EAAT3 inhibitors are psychiatric disorders such as schizophrenia, bipolar disorder, obsessive-compulsive disorder or autism spectrum disorder.

The present invention relates to compounds of formula I and to their pharmaceutically acceptable salts, to their use in the treatment of psychiatric disorders such as schizophrenia, bipolar disorder, obsessive-compulsive disorder or autism spectrum disorder, to compounds of formulas I, IA, IB, IC, ID, IE, IF, IG, IH and IJ as pharmaceutically active substances, to the processes for their production as well as to their use in the treatment or prevention of disorders, relating to EAAT3 inhibitors, such as schizophrenia, bipolar disorder, obsessive-compulsive disorder or autism spectrum disorder and to pharmaceutical compositions containing the compounds of formula IA A further object of the present invention is a method for the treatment or prophylaxis of psychiatric disorder such as schizophrenia, bipolar disorder, obsessive-compulsive disorder or autism spectrum disorder, which method comprises administering an effective amount of a compound of formula I to a mammal in need.

Furthermore, the invention includes all racemic mixtures, all their corresponding enantiomers and/or optical isomers, or analogues containing isotopes of hydrogen, fluorine, carbon, oxygen or nitrogen.

One object of the present invention are novel compounds of formula IA,

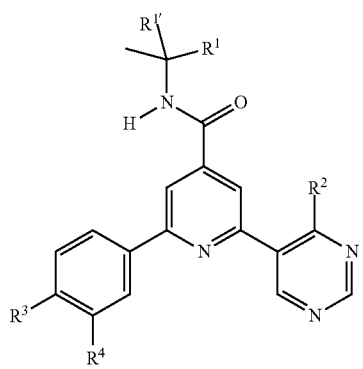

IA wherein
$R^{1'}$ is methyl;
$R^1$ is methyl, ethyl, $CF_3$, $CH_2OH$, cyclopropyl or cyano, or
$R^{1'}$ and $R^1$ may form together a 1,1-dioxo-tetrahydro-thiophen-3-yl ring;
$R^2$ is hydrogen, methyl, ethyl, isopropyl, tert-butyl, cyclopropyl, cyclopropylmethyl, or hydroxmethyl;
$R^3$ is Cl, F, $CF_3$, methyl, methoxy, or cyclopropyl;
$R^4$ is hydrogen, methyl, F or Cl;
or a pharmaceutically acceptable salt or acid addition salt, a racemic mixture, or its corresponding enantiomer and/or optical isomer and/or stereoisomer, for example the following compounds N-tert-Butyl-2-(4-chlorophenyl)-6-(4-propan-2-yl-pyrimidin-5-yl)-pyridine-4-carboxamide
N-tert-Butyl-2-(4-fluorophenyl)-6-(4-propan-2-yl-pyrimidin-5-yl)-pyridine-4-carboxamide
N-tert-Butyl-2-(4-propan-2-yl-pyrimidin-5-yl)-6-[4-(trifluoromethyl)-phenyl]-pyridine-4-carboxamide
N-tert-Butyl-2-(4-methylphenyl)-6-(4-propan-2-yl-pyrimidin-5-yl)-pyridine-4-carboxamide
N-tert-Butyl-2-(3,4-difluorophenyl)-6-(4-propan-2-yl-pyrimidin-5-yl)-pyridine-4-carboxamide
N-tert-Butyl-2-(4-fluoro-3-methylphenyl)-6-(4-propan-2-yl-pyrimidin-5-yl)-pyridine-4-carboxamide
N-tert-Butyl-2-(4-chloro-3-fluorophenyl)-6-(4-propan-2-yl-pyrimidin-5-yl)-pyridine-4-carboxamide
N-tert-Butyl-2-(4-cyclopropyl-phenyl)-6-(4-propan-2-yl-pyrimidin-5-yl)-pyridine-4-carboxamide
2-(4-Chlorophenyl)-N-(2-cyclopropyl-propan-2-yl)-6-(4-propan-2-yl-pyrimidin-5-yl)-pyridine-4-carboxamide
2-(4-Chlorophenyl)-N-(2-cyanopropan-2-yl)-6-(4-propan-2-yl-pyrimidin-5-yl)-pyridine-4-carboxamide
2-(4-Chlorophenyl)-N-(1-hydroxy-2-methylpropan-2-yl)-6-(4-propan-2-yl-pyrimidin-5-yl)-pyridine-4-carboxamide
2-(4-Chlorophenyl)-6-(4-propan-2-yl-pyrimidin-5-yl)-N-(1,1,1-trifluoro-2-methylpropan-2-yl)-pyridine-4-carboxamide
N-tert-Butyl-2-(4-methoxyphenyl)-6-(4-propan-2-yl-pyrimidin-5-yl)-pyridine-4-carboxamide
N-tert-Butyl-2-(3-fluoro-4-methylphenyl)-6-(4-propan-2-yl-pyrimidin-5-yl)-pyridine-4-carboxamide
(RS)-2-(4-Fluorophenyl)-N-(3-methyl-1,1-dioxothiolan-3-yl)-6-(4-propan-2-yl-pyrimidin-5-yl)-pyridine-4-carboxamide
2-(4-Fluorophenyl)-N-(2-methylbutan-2-yl)-6-(4-propan-2-yl-pyrimidin-5-yl)-pyridine-4-carboxamide
N-tert-Butyl-2-(4-ethyl-pyrimidin-5-yl)-6-(4-fluorophenyl)-pyridine-4-carboxamide
N-tert-Butyl-2-(4-fluorophenyl)-6-(4-methylpyrimidin-5-yl)-pyridine-4-carboxamide
N-tert-Butyl-2-(4-cyclopropylpyrimidin-5-yl)-6-(4-fluorophenyl)-pyridine-4-carboxamide
N-tert-Butyl-2-(4-tert-butyl-pyrimidin-5-yl)-6-(4-fluorophenyl)-pyridine-4-carboxamide
N-tert-Butyl-2-(4-tert-butylpyrimidin-5-yl)-6-(4-chlorophenyl)-pyridine-4-carboxamide or
N-tert-Butyl-2-(4-tert-butyl-pyrimidin-5-yl)-6-[4-(trifluoromethyl)-phenyl]-pyridine-4-carboxamide.

One object of the present invention are novel compounds of formula IB,

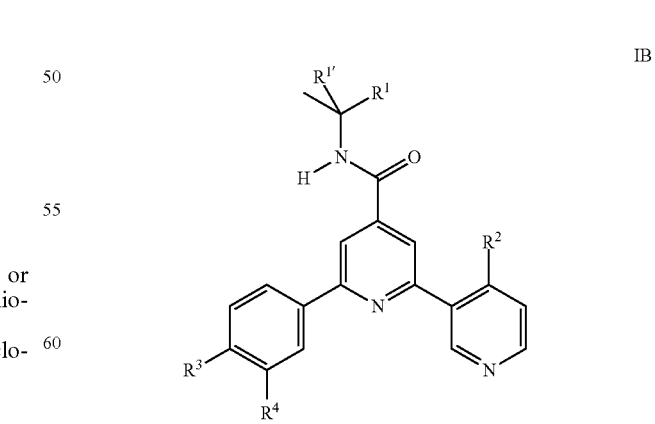

IB wherein
$R^{1'}$ is methyl;
$R^1$ is methyl, ethyl, $CF_3$, $CH_2OH$, cyclopropyl or cyano, or R$^{1'}$ and R$^1$ may form together a 1,1-dioxo-tetrahydro-thiophen-3-yl ring;
R$^2$ is hydrogen, methyl, ethyl, isopropyl, tert-butyl, cyclopropyl, cyclopropylmethyl, or hydroxmethyl;
R$^3$ is Cl, F, CF$_3$, methyl, methoxy, or cyclopropyl;
R$^4$ is hydrogen, methyl, F or Cl;
or a pharmaceutically acceptable salt or acid addition salt, a racemic mixture, or its corresponding enantiomer and/or optical isomer and/or stereoisomer, for example the following compounds N-tert-Butyl-2-(4-fluorophenyl)-6-(4-methylpyridin-3-yl)-pyridine-4-carboxamide
N-tert-Butyl-2-(4-chlorophenyl)-6-(4-methylpyridin-3-yl)-pyridine-4-carboxamide
N-tert-Butyl-2-(4-propan-2-yl-pyridin-3-yl)-6-[4-(trifluoromethyl)-phenyl]-pyridine-4-carboxamide
N-tert-Butyl-2-(4-chlorophenyl)-6-(4-propan-2-yl-pyridin-3-yl)-pyridine-4-carboxamide or
N-tert-Butyl-2-(4-fluorophenyl)-6-(4-propan-2-yl-pyridin-3-yl)-pyridine-4-carboxamide.

One object of the present invention are novel compounds of formula IC,

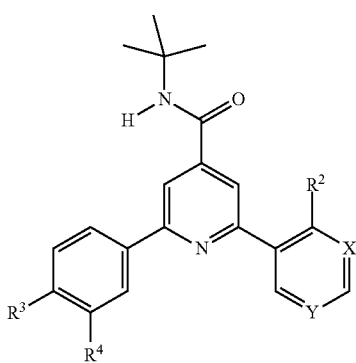

IC wherein
R$^2$ is hydrogen, methyl, ethyl, isopropyl, tert-butyl, cyclopropyl, cyclopropylmethyl, or hydroxmethyl;
R$^3$ is Cl, F, CF$_3$, methyl, methoxy, or cyclopropyl;
R$^4$ is hydrogen, methyl, F or Cl;
X is N or CH;
Y is N or CH;
with the proviso that X and Y are not simultaneously CH;
or a pharmaceutically acceptable salt or acid addition salt, a racemic mixture, or its corresponding enantiomer and/or optical isomer and/or stereoisomer, for example the following compounds N-tert-Butyl-2-(4-chlorophenyl)-6-(4-propan-2-yl-pyrimidin-5-yl)-pyridine-4-carboxamide
N-tert-Butyl-2-(4-fluorophenyl)-6-(4-propan-2-yl-pyrimidin-5-yl)-pyridine-4-carboxamide
N-tert-Butyl-2-(4-propan-2-yl-pyrimidin-5-yl)-6-[4-(trifluoromethyl)-phenyl]-pyridine-4-carboxamide
N-tert-Butyl-2-(4-fluorophenyl)-6-(4-methylpyridin-3-yl)-pyridine-4-carboxamide
N-tert-Butyl-2-(4-chlorophenyl)-6-(4-methylpyridin-3-yl)-pyridine-4-carboxamide
N-tert-Butyl-2-(4-methylphenyl)-6-(4-propan-2-yl-pyrimidin-5-yl)-pyridine-4-carboxamide
N-tert-Butyl-2-(3,4-difluorophenyl)-6-(4-propan-2-yl-pyrimidin-5-yl)-pyridine-4-carboxamide
N-tert-Butyl-2-(4-fluoro-3-methylphenyl)-6-(4-propan-2-yl-pyrimidin-5-yl)-pyridine-4-carboxamide
N-tert-Butyl-2-(4-chloro-3-fluorophenyl)-6-(4-propan-2-yl-pyrimidin-5-yl)-pyridine-4-carboxamide N-tert-Butyl-2-(4-cyclopropyl-phenyl)-6-(4-propan-2-yl-pyrimidin-5-yl)-pyridine-4-carboxamide
N-tert-Butyl-2-(4-ethyl-pyrimidin-5-yl)-6-(4-fluorophenyl)-pyridine-4-carboxamide
N-tert-Butyl-2-(4-fluorophenyl)-6-(4-methylpyrimidin-5-yl)-pyridine-4-carboxamide
N-tert-Butyl-2-(4-methoxyphenyl)-6-(4-propan-2-yl-pyrimidin-5-yl)-pyridine-4-carboxamide
N-tert-Butyl-2-(3-fluoro-4-methylphenyl)-6-(4-propan-2-yl-pyrimidin-5-yl)-pyridine-4-carboxamide
N-tert-Butyl-2-(4-cyclopropylpyrimidin-5-yl)-6-(4-fluorophenyl)-pyridine-4-carboxamide
N-tert-Butyl-2-(4-tert-butyl-pyrimidin-5-yl)-6-(4-fluorophenyl)-pyridine-4-carboxamide
N-tert-Butyl-2-(4-tert-butylpyrimidin-5-yl)-6-(4-chlorophenyl)-pyridine-4-carboxamide
N-tert-Butyl-2-(4-tert-butyl-pyrimidin-5-yl)-6-[4-(trifluoromethyl)-phenyl]-pyridine-4-carboxamide
N-tert-Butyl-2-(4-propan-2-yl-pyridin-3-yl)-6-[4-(trifluoromethyl)-phenyl]-pyridine-4-carboxamide
N-tert-Butyl-2-(4-chlorophenyl)-6-(4-propan-2-yl-pyridin-3-yl)-pyridine-4-carboxamide or
N-tert-Butyl-2-(4-fluorophenyl)-6-(4-propan-2-yl-pyridin-3-yl)-pyridine-4-carboxamide.

One object of the present invention are novel compounds of formula ID,

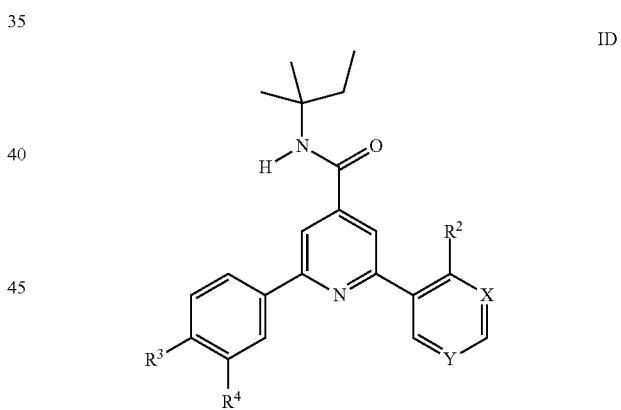

ID wherein
R$^2$ is hydrogen, methyl, ethyl, isopropyl, tert-butyl, cyclopropyl, cyclopropylmethyl, or hydroxmethyl;
R$^3$ is Cl, F, CF$_3$, methyl, methoxy, or cyclopropyl;
R$^4$ is hydrogen, methyl, F or Cl;
X is N or CH;
Y is N or CH;
with the proviso that X and Y are not simultaneously CH;
or a pharmaceutically acceptable salt or acid addition salt, a racemic mixture, or its corresponding enantiomer and/or optical isomer and/or stereoisomer, for example the following compound 2-(4-Fluorophenyl)-N-(2-methylbutan-2-yl)-6-(4-propan-2-yl-pyrimidin-5-yl)-pyridine-4-carboxamide.

One object of the present invention are novel compounds of formula IE,

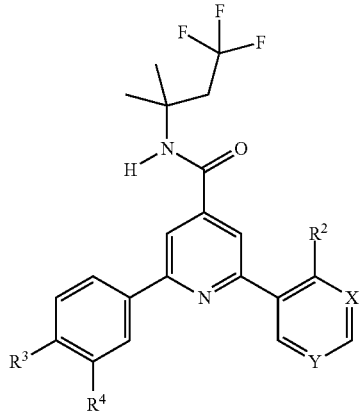

IE wherein
R² is hydrogen, methyl, ethyl, isopropyl, tert-butyl, cyclopropyl, cyclopropylmethyl, or hydroxmethyl;
R³ is Cl, F, CF₃, methyl, methoxy, or cyclopropyl;
R⁴ is hydrogen, methyl, F or Cl;
X is N or CH;
Y is N or CH;
with the proviso that X and Y are not simultaneously CH;
or a pharmaceutically acceptable salt or acid addition salt, a racemic mixture, or its corresponding enantiomer and/or optical isomer and/or stereoisomer, for example the following compound
2-(4-Chlorophenyl)-6-(4-propan-2-yl-pyrimidin-5-yl)-N-(1,1,1-trifluoro-2-methylpropan-2-yl)-pyridine-4-carboxamide One object of the present invention are novel compounds of formula IF,

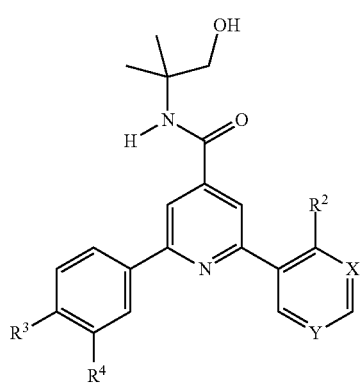

IF wherein
R² is hydrogen, methyl, ethyl, isopropyl, tert-butyl, cyclopropyl, cyclopropylmethyl, or hydroxmethyl;
R³ is Cl, F, CF₃, methyl, methoxy, or cyclopropyl;
R⁴ is hydrogen, methyl, F or Cl;
X is N or CH;
Y is N or CH;
with the proviso that X and Y are not simultaneously CH;
or a pharmaceutically acceptable salt or acid addition salt, a racemic mixture, or its corresponding enantiomer and/or optical isomer and/or stereoisomer, for example the following compound
2-(4-Chlorophenyl)-N-(1-hydroxy-2-methylpropan-2-yl)-6-(4-propan-2-yl-pyrimidin-5-yl)-pyridine-4-carboxamide One object of the present invention are novel compounds of formula IG,

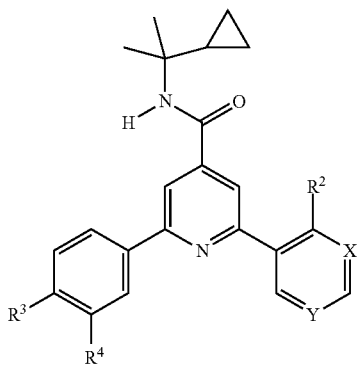

IG wherein
R² is hydrogen, methyl, ethyl, isopropyl, tert-butyl, cyclopropyl, cyclopropylmethyl, or hydroxmethyl;
R³ is Cl, F, CF₃, methyl, methoxy, or cyclopropyl;
R⁴ is hydrogen, methyl, F or Cl;
X is N or CH;
Y is N or CH;
with the proviso that X and Y are not simultaneously CH;
or a pharmaceutically acceptable salt or acid addition salt, a racemic mixture, or its corresponding enantiomer and/or optical isomer and/or stereoisomer, for example the following compound
2-(4-Chlorophenyl)-N-(2-cyclopropyl-propan-2-yl)-6-(4-propan-2-yl-pyrimidin-5-yl)-pyridine-4-carboxamide One object of the present invention are novel compounds of formula IH,

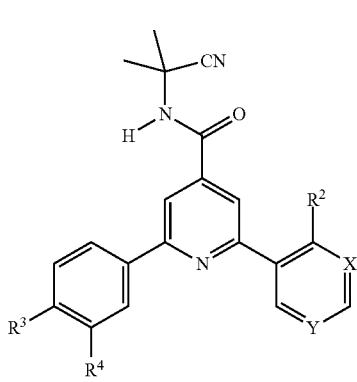

IH wherein
R² is hydrogen, methyl, ethyl, isopropyl, tert-butyl, cyclopropyl, cyclopropylmethyl, or hydroxmethyl;
R³ is Cl, F, CF₃, methyl, methoxy, or cyclopropyl;
R⁴ is hydrogen, methyl, F or Cl;
X is N or CH;
Y is N or CH;
with the proviso that X and Y are not simultaneously CH;
or a pharmaceutically acceptable salt or acid addition salt, a racemic mixture, or its corresponding enantiomer and/or optical isomer and/or stereoisomer, for example the following compound 2-(4-Chlorophenyl)-N-(2-cyclopropyl-propan-2-yl)-6-(4-propan-2-yl-pyrimidin-5-yl)-pyridine-4-carboxamide.

One object of the present invention are novel compounds of formula IJ,

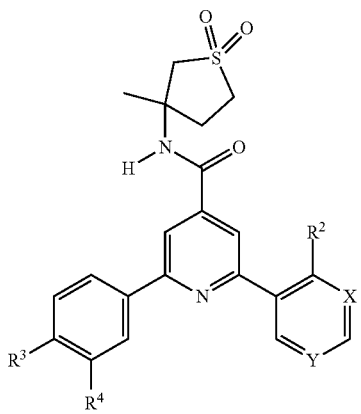

wherein
R² is hydrogen, methyl, ethyl, isopropyl, tert-butyl, cyclopropyl, cyclopropylmethyl, or hydroxmethyl;
R³ is Cl, F, CF₃, methyl, methoxy, or cyclopropyl;
R⁴ is hydrogen, methyl, F or Cl;
X is N or CH;
Y is N or CH;
with the proviso that X and Y are not simultaneously CH;
or a pharmaceutically acceptable salt or acid addition salt, a racemic mixture, or its corresponding enantiomer and/or optical isomer and/or stereoisomer, for example the following compound
(RS)-2-(4-Fluorophenyl)-N-(3-methyl-1,1-dioxothiolan-3-yl)-6-(4-propan-2-yl-pyrimidin-5-yl)-pyridine-4-carboxamide.

The preparation of compounds of formulas I, IA, IB, IC, ID, IE, IF, IG, IH and IJ of the present invention may be carried out in sequential or convergent synthetic routes. Syntheses of the compounds of the invention are shown in the following schemes 1 to 5. The skills required for carrying out the reaction and purification of the resulting products are known to those skilled in the art. The substituents and indices used in the following description of the processes have the significance given herein before.

The compounds of formulas I, IA, IB, IC, ID, IE, IF, IG, IH and IJ can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of I, IA, IB, IC, ID, IE, IF, IG, IH and IJ and their pharmaceutically acceptable salts may be prepared by methods, known in the art, for example by the process variant described below, which process comprises a) reacting a compound of formula

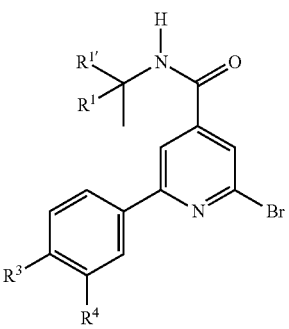

with a compound of formula

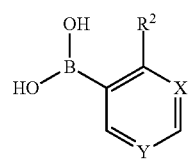

to a compound of formula I

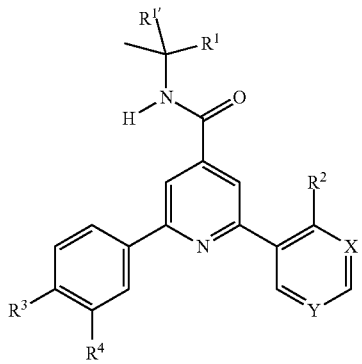

wherein the substituents are as described above, or if desired, converting the compounds obtained into pharmaceutically acceptable acid addition salts.

b) reacting a compound of formula

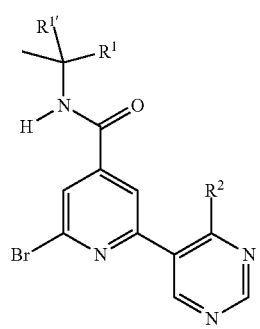

with a compound of formula

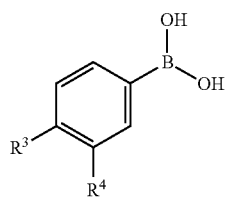

to a compound of formula I

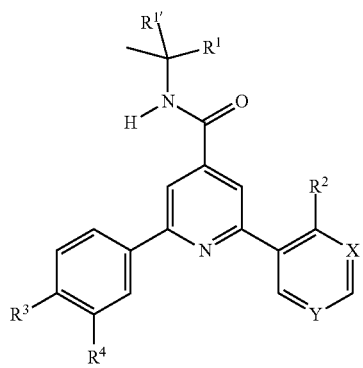

wherein the substituents are described above, or
if desired, converting the compounds obtained into pharmaceutically acceptable acid addition salts.

The preparation of compounds of formulas I, IA, IB, IC, ID, IE, IF, IG, IH and IJ is further described in more detail in scheme 1 to 5 and in examples 1-27.

The pyridine or pyrimidine derivatives I can either be prepared from the intermediate bromo derivatives II by coupling reaction with commercially available pyridine and pyrimidine boronic acids III.

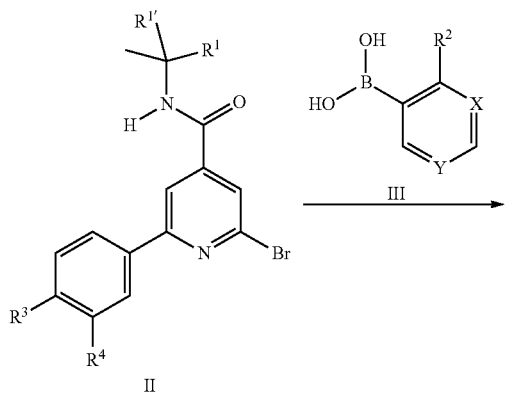

or by coupling reaction of the bromo derivatives IV with commercially available boronic acid derivatives V.

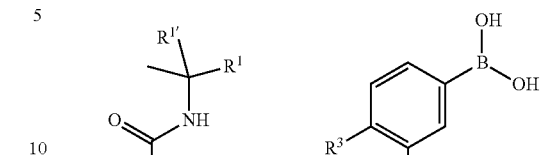

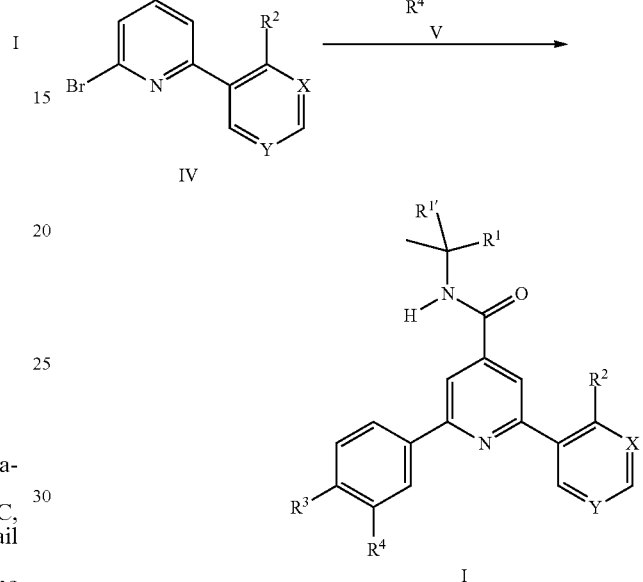

The bromo derivatives II can be prepared starting from commercially available 2,6-dibromo-isonicotinic acid VI. Amide formation with the commercially available amines VII using standard conditions leads to the amides VIII which can be coupled with commercially available boronic acid derivatives V to yield the final building blocks II.

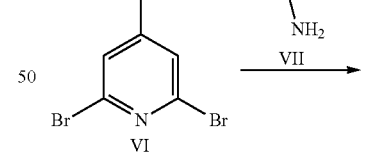

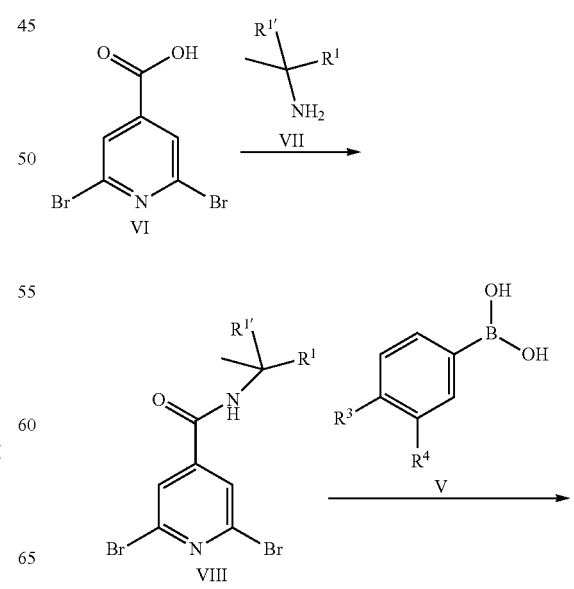

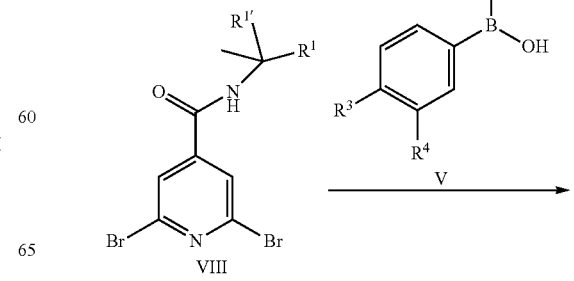

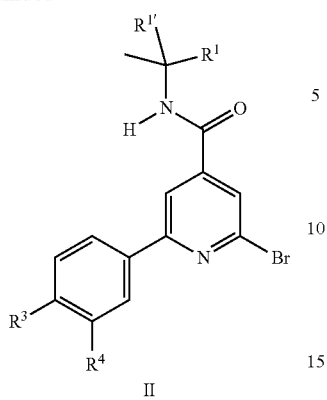

II

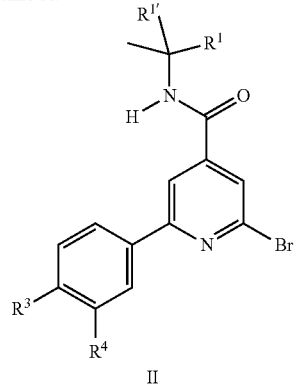

II

An alternative route for the synthesis of the bromo derivatives II can start from commercially available methyl 2-bromo-isonicotinate IX which can be coupled with the commercially available boronic acid derivatives V to yield the 2-aryl-pyridine derivatives X which can be transformed by standard procedures into the bromo derivatives XI. Saponification and subsequent amide formation with the commercially available amines VII yield the building blocks II.

The synthesis of the bromo derivatives IV can be performed starting from the above described amides VIII which can be coupled with the commercially available pyridine and pyrimidine boronic acids III to yield the building blocks IV.

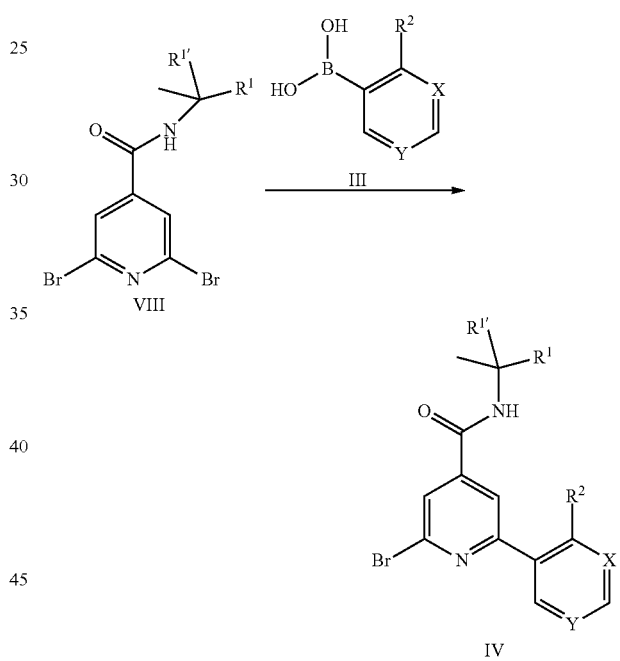

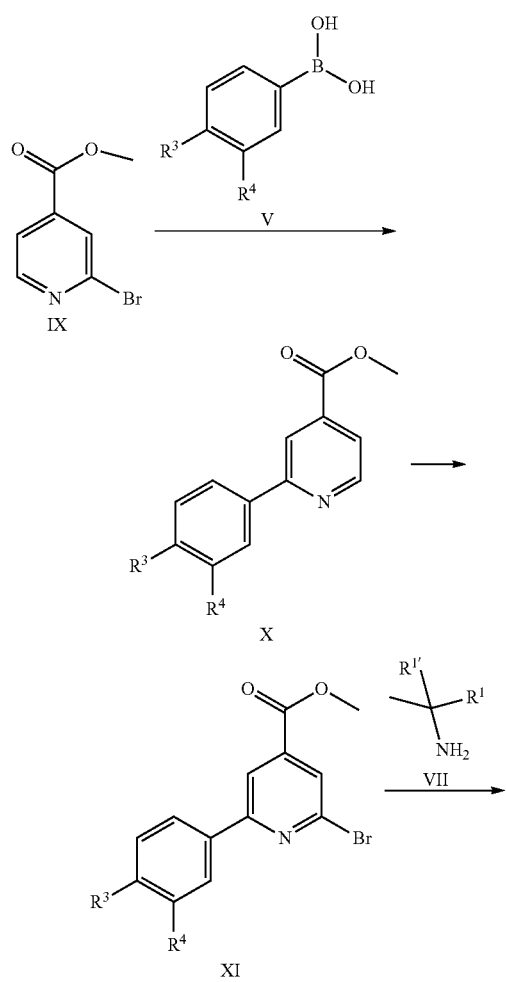

Generally speaking, the sequence of steps used to synthesize the compounds of formula I can also be modified in certain cases.

The compounds of formula I and their pharmaceutically usable addition salts possess valuable pharmaceutical properties. Specifically, it has been found that the compounds of the present invention are EAAT3 inhibitors for use in the treatment of schizophrenia, bipolar disorder, obsessive-compulsive disorder or autism spectrum disorders.

The compounds were investigated in accordance with the test given hereinafter.

Biological Assay and Data

The FLIPR Membrane Potential (FMP) Assay

HEK-293 cells stably expressing human EAAT3 were seeded at 55 000 cells/well in growth medium (DMEM glutamate free (Invitrogen 11960-044), 1% Pen Strep (10 ml/l GIBCO BRL No 15140-023), 10% FCS non dialysed heat inactivated, 5 mg/l puromycin) in poly-D-lysine treated 96-well black microtiter plates with clear-bottom. After 24 h, the growth medium was removed and 100 μl/well of Krebs buffer (140 mM NaCl, 4.7 mM KCl, 2.5 mM $CaCl_2$, 1.2 mM $MgCl_2$, 11 mM HEPES, 10 mM D-glucose, pH=7.4) added. The cells were then loaded by adding 100 μl/well FMP assay dye (FLIPR Membrane Potential assay reagent, Molecular Devices). The 96-well plates were then incubated at 37° C. for 1 h. The depolarization of the cells will cause more dye to enter in the cells, where it will bind to intracellular proteins and lipids and cause an increase in the fluorescence signal. Antagonist potency at human EAAT3 was determined by using L-glutamate as agonist at a concentration which gives 80% of the maximum response. The antagonists were applied 15 min before the application of the agonist L-glutamate. The assays were performed at room temperature and measurements done by using a Fluorometric Imaging Plate Reader (FLIPR, Molecular Devices) and filter #2. Responses were measured as peak increase in fluorescence minus basal (i.e. fluorescence without addition of L-glutamate). Kb was determined using the Cheng-Prusoff equation $Kb=IC_{50}/[1+(A/EC_{50})]$, where $IC_{50}$ is the concentration of the antagonist producing 50% inhibition, A is the concentration of the agonist against which the $IC_{50}$ is being determined (at $EC_{80}$) and $EC_{50}$ is the concentration of the agonist producing 50% inhibition.

LIST OF EXAMPLES AND DATA

| | Structure | Compound name | EAAT3 Kb [μM] |
|---|---|---|---|
| 1 | 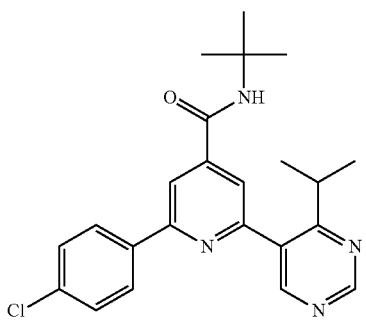 [SMILES: CC(C)c1ncncc1-c1cc(C(=O)NC(C)(C)C)cc(-c2ccc(Cl)cc2)n1] | N-tert-Butyl-2-(4-chlorophenyl)-6-(4-propan-2-yl-pyrimidin-5-yl)-pyridine-4-carboxamide | 0.1 |
| 2 | 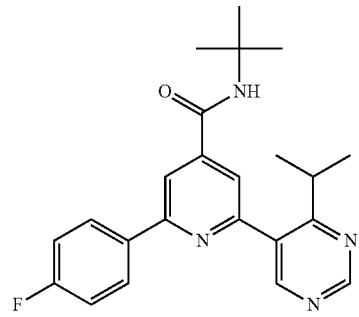 [SMILES: CC(C)c1ncncc1-c1cc(C(=O)NC(C)(C)C)cc(-c2ccc(F)cc2)n1] | N-tert-Butyl-2-(4-fluorophenyl)-6-(4-propan-2-yl-pyrimidin-5-yl)-pyridine-4-carboxamide | 0.12 |
| 3 | 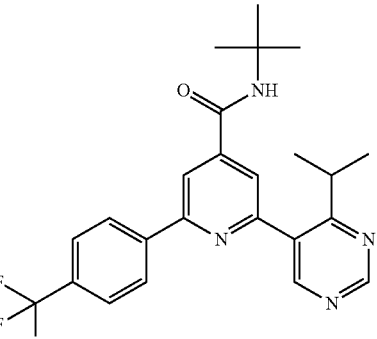 | N-tert-Butyl-2-(4-propan-2-yl-pyrimidin-5-yl)-6-[4-(trifluoromethyl)phenyl]-pyridine-4-carboxamide | 0.11 |

-continued
| | Structure | Compound name | EAAT3 Kb [μM] |
|---|---|---|---|
| 4 | 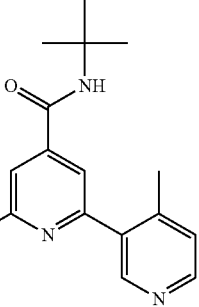 | N-tert-Butyl-2-(4-fluorophenyl)-6-(4-methylpyridin-3-yl)-pyridine-4-carboxamide | 0.26 |
| 5 | 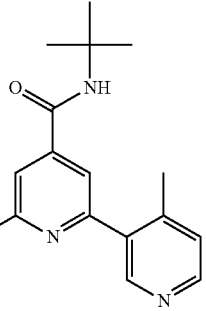 | N-tert-Butyl-2-(4-chlorophenyl)-6-(4-methylpyridin-3-yl)-pyridine-4-carboxamide | 0.22 |
| 6 | 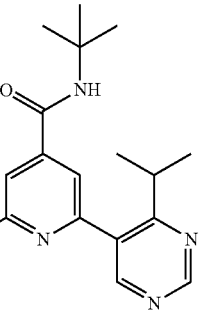 | N-tert-Butyl-2-(4-methylphenyl)-6-(4-propan-2-yl-pyrimidin-5-yl)-pyridine-4-carboxamide | 0.14 |
| 7 | 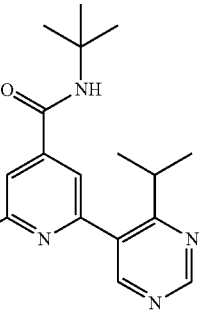 | N-tert-Butyl-2-(3,4-difluorophenyl)-6-(4-propan-2-yl-pyrimidin-5-yl)-pyridine-4-carboxamide | 0.11 |

-continued

| | Structure | Compound name | EAAT3 Kb [μM] |
|---|---|---|---|
| 8 | 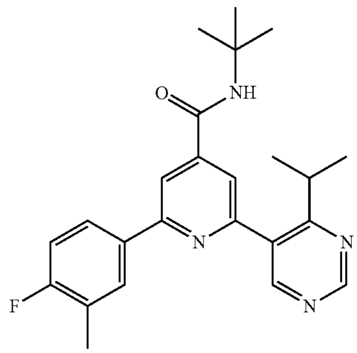 [SMILES: Cc1cc(-c2cc(C(=O)NC(C)(C)C)cc(-c3cncnc3C(C)C)n2)ccc1F] | N-tert-Butyl-2-(4-fluoro-3-methyl-phenyl)-6-(4-propan-2-yl-pyrimidin-5-yl)-pyridine-4-carboxamide | 0.26 |
| 9 | 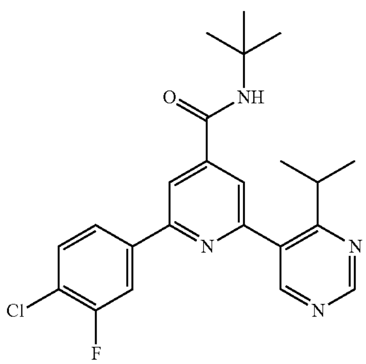 [SMILES: CC(C)c1ncncc1-c1cc(C(=O)NC(C)(C)C)cc(-c2ccc(Cl)c(F)c2)n1] | N-tert-Butyl-2-(4-chloro-3-fluoro-phenyl)-6-(4-propan-2-yl-pyrimidin-5-yl)-pyridine-4-carboxamide | 0.26 |
| 10 | 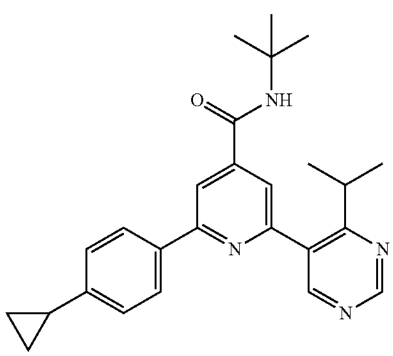 [SMILES: CC(C)c1ncncc1-c1cc(C(=O)NC(C)(C)C)cc(-c2ccc(C3CC3)cc2)n1] | N-tert-Butyl-2-(4-cyclopropyl-phenyl)-6-(4-propan-2-yl-pyrimidin-5-yl)-pyridine-4-carboxamide | 0.29 |
| 11 | 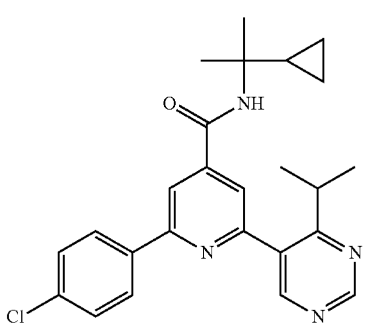 [SMILES: CC(C)c1ncncc1-c1cc(C(=O)NC(C)(C)C2CC2)cc(-c2ccc(Cl)cc2)n1] | 2-(4-Chlorophenyl)-N-(2-cyclopropyl-propan-2-yl)-6-(4-propan-2-yl-pyrimidin-5-yl)-pyridine-4-carboxamide | 0.15 |

-continued

| | Structure | Compound name | EAAT3 Kb [μM] |
|---|---|---|---|
| 12 | 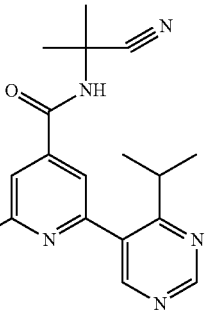 | 2-(4-Chlorophenyl)-N-(2-cyanopropan-2-yl)-6-(4-propan-2-yl-pyrimidin-5-yl)-pyridine-4-carboxamide | 0.47 |
| 13 | 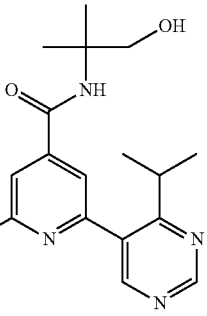 | 2-(4-Chlorophenyl)-N-(1-hydroxy-2-methylpropan-2-yl)-6-(4-propan-2-yl-pyrimidin-5-yl)-pyridine-4-carboxamide | 0.2 |
| 14 | 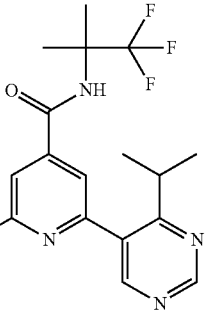 | 2-(4-Chlorophenyl)-6-(4-propan-2-yl-pyrimidin-5-yl)-N-(1,1,1-trifluoro-2-methylpropan-2-yl)-pyridine-4-carboxamide | 0.27 |
| 15 | 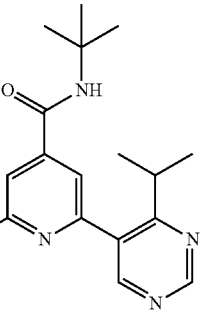 | N-tert-Butyl-2-(4-methoxyphenyl)-6-(4-propan-2-yl-pyrimidin-5-yl)-pyridine-4-carboxamide | 0.31 |

-continued
| | Structure | Compound name | EAAT3 Kb [μM] |
|---|---|---|---|
| 16 | 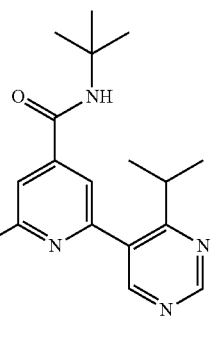 | N-tert-Butyl-2-(3-fluoro-4-methyl-phenyl)-6-(4-propan-2-yl-pyrimidin-5-yl)-pyridine-4-carboxamide | 0.25 |
| 17 | 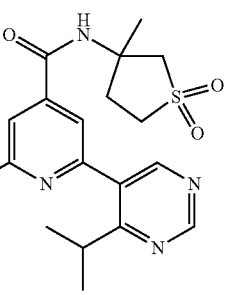 | (RS)-2-(4-Fluoro-phenyl)-N-(3-methyl-1,1-dioxothiolan-3-yl)-6-(4-propan-2-yl-pyrimidin-5-yl)-pyridine-4-carboxamide | 0.27 |
| 18 | 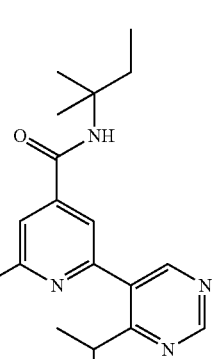 | 2-(4-Fluorophenyl)-N-(2-methylbutan-2-yl)-6-(4-propan-2-yl-pyrimidin-5-yl)-pyridine-4-carboxamide | 0.12 |
| 19 | 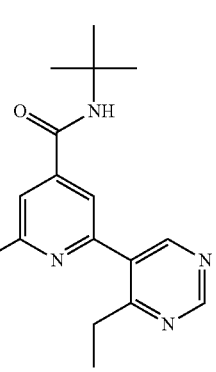 | N-tert-Butyl-2-(4-ethyl-pyrimidin-5-yl)-6-(4-fluoro-phenyl)-pyridine-4-carboxamide | 0.18 |

-continued
| | Structure | Compound name | EAAT3 Kb [µM] |
|---|---|---|---|
| 20 | 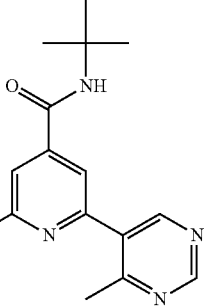 | N-tert-Butyl-2-(4-fluorophenyl)-6-(4-methyl-pyrimidin-5-yl)-pyridine-4-carboxamide | 0.48 |
| 21 | 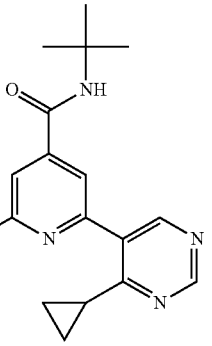 | N-tert-Butyl-2-(4-cyclopropyl-pyrimidin-5-yl)-6-(4-fluorophenyl)-pyridine-4-carboxamide | 0.56 |
| 22 | 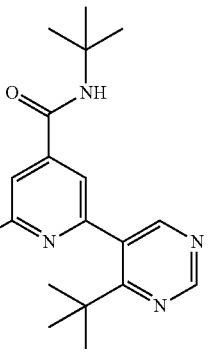 | N-tert-Butyl-2-(4-tert-butyl-pyrimidin-5-yl)-6-(4-fluoro-phenyl)-pyridine-4-carboxamide | 0.063 |
| 23 | 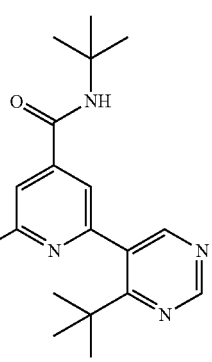 | N-tert-Butyl-2-(4-tert-butylpyrimidin-5-yl)-6-(4-chloro-phenyl)-pyridine-4-carboxamide | 0.14 |

| | Structure | Compound name | EAAT3 Kb [μM] |
|---|---|---|---|
| 24 | 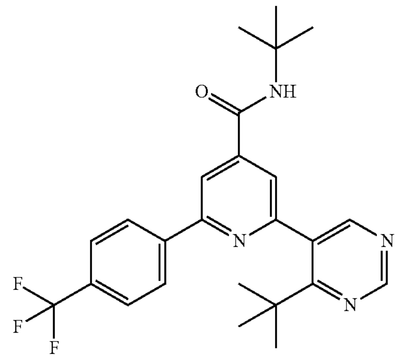 [SMILES: CC(C)(C)NC(=O)c1cc(-c2ccc(C(F)(F)F)cc2)nc(-c2cncnc2C(C)(C)C)c1] | N-tert-Butyl-2-(4-tert-butyl-pyrimidin-5-yl)-6-[4-(trifluoro-methyl)-phenyl]-pyridine-4-carboxamide | 0.29 |
| 25 | 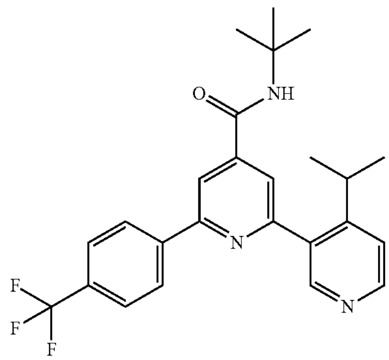 [SMILES: CC(C)c1ccncc1-c1cc(C(=O)NC(C)(C)C)cc(-c2ccc(C(F)(F)F)cc2)n1] | N-tert-Butyl-2-(4-propan-2-yl-pyridin-3-yl)-6-[4-(trifluoro-methyl)-phenyl]-pyridine-4-carboxamide | 0.35 |
| 26 | 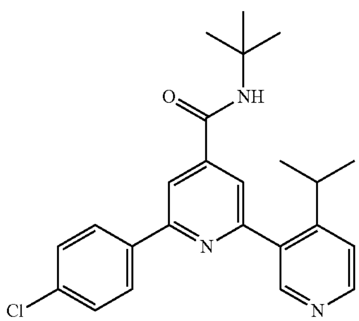 [SMILES: CC(C)c1ccncc1-c1cc(C(=O)NC(C)(C)C)cc(-c2ccc(Cl)cc2)n1] | N-tert-Butyl-2-(4-chlorophenyl)-6-(4-propan-2-yl-pyridin-3-yl)-pyridine-4-carboxamide | 0.31 |
| 27 | 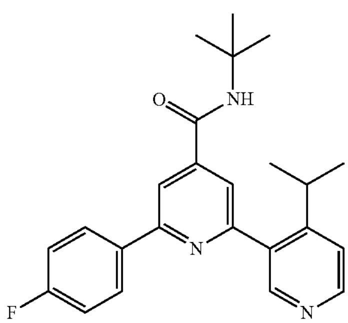 [SMILES: CC(C)c1ccncc1-c1cc(C(=O)NC(C)(C)C)cc(-c2ccc(F)cc2)n1] | N-tert-Butyl-2-(4-fluorophenyl)-6-(4-propan-2-yl-pyridin-3-yl)-pyridine-4-carboxamide | 0.17 |

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Preparation of Pharmaceutical Compositions Comprising Compounds of the Invention:

Tablets of the following composition are manufactured in the usual manner:

|  | mg/tablet | | | |
| --- | --- | --- | --- | --- |
| ingredient | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules of the following composition are manufactured:

|  | mg/capsule | | | |
| --- | --- | --- | --- | --- |
| ingredient | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

A compound of formula I lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Injection solutions of the following composition are manufactured:

| ingredient | mg/injection solution. |
| --- | --- |
| Compound of formula I | 3 |
| Polyethylene Glycol 400 | 150 |
| acetic acid | q.s. ad pH 5.0 |
| water for injection solutions | ad 1.0 ml |

Manufacturing Procedure

A compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Experimental Section

Intermediates

Intermediate 1: 2-Bromo-N-tert-butyl-6-(4-fluorophenyl)-pyridine-4-carboxamide

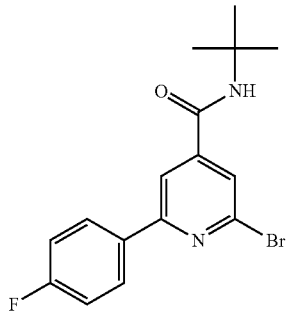 [SMILES: CC(C)(C)NC(=O)c1cc(Br)nc(-c2ccc(F)cc2)c1]

Step A

To a stirred solution of commercially available 2,6-dibromoisonicotinic acid (3 g, 10.7 mmol) in THF (77 ml) was added N,N-diisopropylethylamine (3.45 g, 4.66 ml, 26.7 mmol), commercially available 2-methylpropan-2-amine (956 mg, 1.37 ml, 12.8 mmol) and TBTU (4.46 g, 13.9 mmol). The reaction mixture was allowed to stir for 17 h at room temperature, filtered, evaporated and purified by flash chromatography on silica gel [heptane/ethyl acetate (0-50%)] to yield 2,6-dibromo-N-tert-butylpyridine-4-carboxamide (3.28 g, 91%) as an off-white solid, MS (ISP) m/z=337.0 [(M+H)+], mp 148° C.

Step B

A mixture of 2,6-dibromo-N-tert-butylpyridine-4-carboxamide (3.28 g, 9.76 mmol), commercially available (4-fluorophenyl)-boronic acid (1.37 g, 9.76 mmol), potassium carbonate (1.35 g, 9.76 mmol) and PdCl₂(dppf) (239 mg, 293 µmol) in methanol (39 ml) was heated at 100° C. for 10 min in a microwave reactor. The reaction mixture was filtered and purified by flash chromatography on silica gel [heptane/ethyl acetate 4:1] to give 3.32 g of an off-white solid which was further purified by reverse phase HPLC (acetonitrile/formic acid 98:2) to yield the title compound (1.59 g, 46%) as an off-white solid, MS (ISP) m/z=351.1 [(M+H)+], mp 209° C.

Intermediate 2: 2-Bromo-N-tert-butyl-6-(4-chlorophenyl)-pyridine-4-carboxamide

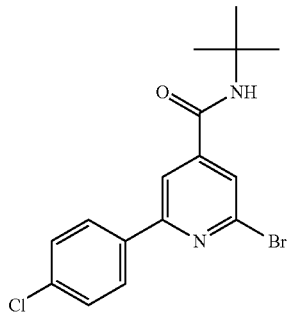 [SMILES: CC(C)(C)NC(=O)c1cc(Br)nc(-c2ccc(Cl)cc2)c1]

The title compound, white solid (0.74 g, 31%), MS (ISP) m/z=369.0 [(M+H)+], mp 208° C., was prepared in accordance with the general method of intermediate 1, step B, from 2,6-dibromo-N-tert-butylpyridine-4-carboxamide (intermediate 1, step A) (2.18 g, 6.49 mmol) and commercially available (4-chlorophenyl)-boronic acid (1.01 g, 6.49 mmol).

Intermediate 3: 2-Bromo-N-tert-butyl-6-[4-(trifluoromethyl)-phenyl]-pyridine-4-carboxamide

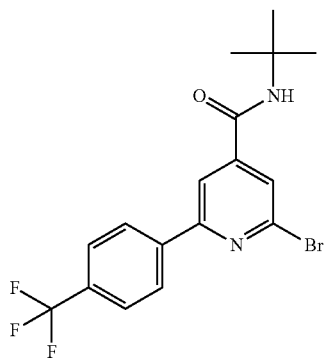 [SMILES: CC(C)(C)NC(=O)c1cc(Br)nc(-c2ccc(C(F)(F)F)cc2)c1]

The title compound, white solid (1.02 g, 40%), MS (ISP) m/z=403.0 [(M+H)+], mp 239° C., was prepared in accordance with the general method of intermediate 1, step B, from 2,6-dibromo-N-tert-butylpyridine-4-carboxamide (intermediate 1, step A) (2.15 g, 6.40 mmol) and commercially available (4-trifluoromethylphenyl)-boronic acid (1.22 g, 6.40 mmol).

Intermediate 4: 2-Bromo-N-tert-butyl-6-(4-propan-2-yl-pyrimidin-5-yl)-pyridine-4-carboxamide

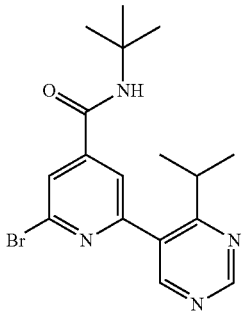 [SMILES: CC(C)c1ncncc1-c1cc(C(=O)NC(C)(C)C)cc(Br)n1]

The title compound, yellow foam (0.57 g, 45%), MS (ISP) m/z=377.1 [(M+H)+], was prepared in accordance with the general method of intermediate 1, step B, from 2,6-dibromo-N-tert-butylpyridine-4-carboxamide (intermediate 1, step A) (1.13 g, 3.37 mmol) and commercially available (4-isopropyl-pyrimidin-5-yl)-boronic acid (0.56 g, 3.37 mmol).

Intermediate 5: 2-Bromo-6-(4-chlorophenyl)-N-(2-cyclopropylpropan-2-yl)-pyridine-4-carboxamide

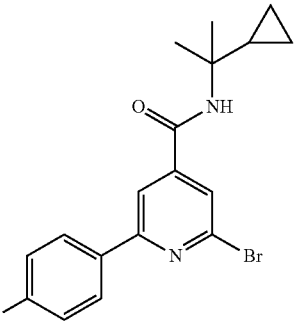

Step A 2,6-Dibromo-N-(2-cyclopropylpropan-2-yl)-pyridine-4-carboxamide, white solid (2.48 g, 96%), MS (ISP) m/z=363.0 [(M+H)+], mp 119° C., was prepared in accordance with the general method of intermediate 1, step A, from commercially available 2,6-dibromo-isonicotinic acid (2.0 g, 7.12 mmol) and commercially available 2-cyclopropylpropan-2-amine hydrochloride (1.16 g, 8.54 mmol).

Step B

The title compound, white solid (0.70 g, 26%), MS (ISP) m/z=395.0 [(M+H)+], mp 185° C., was prepared in accordance with the general method of intermediate 1, step B, from 2,6-dibromo-N-(2-cyclopropylpropan-2-yl)-pyridine- 4-carboxamide (intermediate 5, step A) (2.48 g, 6.85 mmol) and commercially available (4-chlorophenyl)-boronic acid (1.07 g, 6.85 mmol).

Intermediate 6: 2-Bromo-6-(4-chlorophenyl)-N-(1,1,1-trifluoro-2-methylpropan-2-yl)-pyridine-4-carboxamide

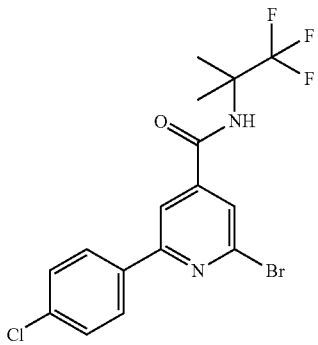 [SMILES: CC(C)(NC(=O)c1cc(Br)nc(-c2ccc(Cl)cc2)c1)C(F)(F)F]

Step A

A mixture of commercially available methyl 2-bromoisonicotinate (3.0 g, 13.9 mmol), commercially available (4-chlorophenyl)-boronic acid (2.61 g, 16.7 mmol), potassium carbonate (2.30 g, 16.7 mmol) and PdCl$_2$(dppf) (340 mg, 417 µmol) in methanol (27 ml) was heated at 100° C. for 10 min in a microwave reactor. The reaction mixture was filtered and purified by flash chromatography on silica gel [heptane/ethyl acetate 4:1] to yield methyl 2-(4-chlorophenyl)-pyridine-4-carboxylate (3.16 g, 92%) as a white solid, MS (ISP) m/z=248.1 [(M+H)$^+$], mp 74° C.

Step B

A stirred solution of methyl 2-(4-chlorophenyl)-pyridine-4-carboxylate (3.15 g, 12.7 mmol) in dichloromethane (36 ml) was cooled to 0° C. in an ice-bath, m-chloro-perbenzoic acid (5.7 g, 25.4 mmol) was added and the reaction mixture was allowed to stir for 17 h at room temperature. 1N NaOH (60 ml) was added and the mixture was extracted with dichloromethane (2×50 ml). The combined organic layers were washed with saturated sodium bicarbonate solution (50 ml) and brine (50 ml), dried (MgSO$_4$) and evaporated to yield methyl 2-(4-chlorophenyl)-1-oxido-1-pyridinium-4-carboxylate (3.15 g, 94%) as an off-white solid, MS (ISP) m/z=264.0 [(M+H)$^+$], mp 135° C.

Step C

A stirred solution of methyl 2-(4-chlorophenyl)-1-oxido-1-pyridinium-4-carboxylate (3.15 g, 11.9 mmol) in toluene (60 ml) was heated to 80° C., phosphorus oxybromide (13.7 g, 47.8 mmol) was added and the reaction mixture was allowed to stir for 2 h at 80° C. The reaction mixture was cooled to room temperature, poured into ice/water (100 ml) and extracted with ethyl acetate (2×70 ml). The combined organic layers were washed with brine (70 ml), dried (MgSO$_4$) and evaporated. The crude product (4.25 g) was further purified by flash chromatography on silica gel (DCM/MeOH 95:5) to yield methyl 2-bromo-6-(4-chlorophenyl)-pyridine-4-carboxylate (1.40 g, 36%) as an off-white solid, MS (ISP) m/z=327.9 [(M+H)$^+$], mp 101° C.

Step D

To a stirred solution of methyl 2-bromo-6-(4-chlorophenyl)-pyridine-4-carboxylate (1.40 g, 4.29 mmol) in THF (7 ml), methanol (7 ml) and water (7 ml), lithium hydroxide monohydrate (234 mg, 5.57 mmol) was added and the reaction mixture was allowed to stir for 3 h at room temperature. The reaction mixture was concentrated to one third, 2N HCl solution (5 ml) was added, the precipitate was collected by filtration, washed with water and dried to yield 2-bromo-6-(4-chlorophenyl)-pyridine-4-carboxylic acid (1.18 g, 88%) as a white solid, MS (ISP) m/z=313.9 [(M+H)$^+$], mp 191° C.

Step E

A stirred solution of 2-bromo-6-(4-chlorophenyl)-pyridine-4-carboxylic acid (500 mg, 1.6 mmol) in THF (12.8 ml) was cooled in an ice bath to 0° C., oxalyl chloride (4.63 g, 3.19 ml, 36.5 mmol) and DMF (64.2 µl) were added, the reaction mixture was allowed to stir for 1 h at room temperature, and evaporated. THF (13 ml), 1,1,1-trifluoro-2-methylpropan-2-amine (244 mg, 220 µl, 1.92 mmol) and N,N-diisopropylethylamine (724 mg, 958 µl, 5.6 mmol) were added, the reaction mixture was allowed to stir for 17 h at room temperature and evaporated. Purification by flash chromatography on silica gel [heptane/ethyl acetate (0-50%)] yielded the title compound (0.58 g, 86%) as an off-white solid, MS (ISN) m/z=421.2 [(M−H)$^−$], mp 192° C.

Intermediate 7: 2-Bromo-6-(4-chlorophenyl)-N-(2-cyanopropan-2-yl)-pyridine-4-carboxamide

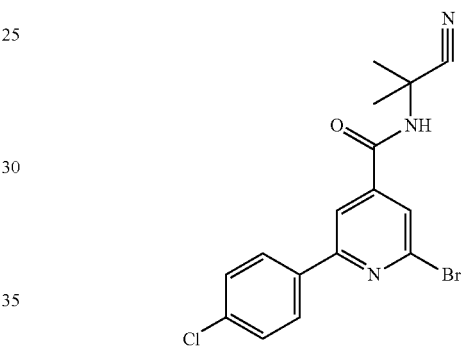

The title compound, light brown foam (352 mg, 93%), MS (ISP) m/z=380.0 [(M+H)$^+$], was prepared in accordance with the general method of intermediate 6, step E, from 2-bromo-6-(4-chlorophenyl)-pyridine-4-carboxylic acid (intermediate 6, step D) (313 mg, 1.0 mmol) and commercially available 2-amino-2-methylpropanenitrile (126 mg, 1.5 mmol).

Intermediate 8: 2-Bromo-6-(4-chlorophenyl)-N-(1-hydroxy-2-methylpropan-2-yl)-pyridine-4-carboxamide

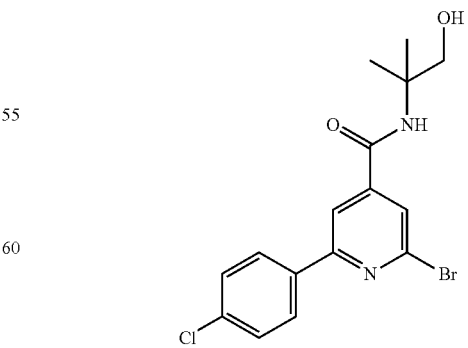

To a stirred solution of 2-bromo-6-(4-chlorophenyl)-pyridine-4-carboxylic acid (intermediate 6, step D) (313 mg, 1.0 mmol) in THF (7.2 ml) was added at room temperature N,N-diisopropylethylamine (323 mg, 437 µl, 2.5 mmol), commercially available 2-amino-2-methylpropan-1-ol (134 mg, 144 µl, 1.5 mmol) and TBTU (514 mg, 1.6 mmol). The reaction mixture was allowed to stir for 17 h at room temperature, filtered and purified by flash chromatography [heptane/ethyl acetate (20-80%)] to yield title compound (284 mg, 74%) as a white solid, MS (ISN) m/z=385.0 [(M+H)⁺], mp 174° C.

Intermediate 9: (RS)-2-Bromo-6-(4-fluorophenyl)-N-(3-methyl-1,1-dioxothiolan-3-yl)-pyridine-4-carboxamide

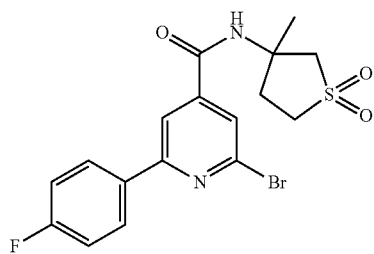 [SMILES: CC1(NC(=O)c2cc(Br)nc(-c3ccc(F)cc3)c2)CCS(=O)(=O)C1]

Step A (RS)-2,6-Dibromo-N-(3-methyl-1,1-dioxothiolan-3-yl)-pyridine-4-carboxamide, white foam (0.97 g, 94%), MS (ISP) m/z=413.0 [(M+H)⁺], was prepared in accordance with the general method of intermediate 1, step A, from commercially available 2,6-dibromo-isonicotinic acid (0.70 g, 2.50 mmol) and commercially available (RS)-3-amino-3-methyltetrahydro-thiophene 1,1-dioxide hydrochloride (0.56 g, 3.0 mmol).

Step B

The title compound, white foam (498 mg, 50%), MS (ISP) m/z=429.0 [(M+H)⁺], was prepared in accordance with the general method of intermediate 1, step B, from (RS)-2,6-dibromo-N-(3-methyl-1,1-dioxothiolan-3-yl)-pyridine-4-carboxamide (0.96 g, 2.33 mmol) and commercially available (4-fluorophenyl)-boronic acid (326 mg, 2.33 mmol).

Intermediate 10: 2-Bromo-6-(4-fluorophenyl)-N-(2-methylbutan-2-yl)-pyridine-4-carboxamide

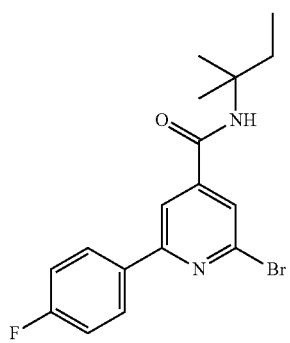 [SMILES: CCC(C)(C)NC(=O)c1cc(Br)nc(-c2ccc(F)cc2)c1]

Step A 2,6-Dibromo-N-(2-methylbutan-2-yl)-pyridine-4-carboxamide, light brown solid (0.79 g, 90%), MS (ISP) m/z=351.0 [(M+H)⁺], mp 92° C., was prepared in accordance with the general method of intermediate 1, step A, from commercially available 2,6-dibromo-isonicotinic acid (0.70 g, 2.50 mmol) and commercially available 2-methylbutan-2-amine (0.26 g, 3.0 mmol).

Step B

The title compound, white solid (303 mg, 37%), MS (ISP) m/z=367.1 [(M+H)⁺], mp 193° C., was prepared in accordance with the general method of intermediate 1, step B, from 2,6-dibromo-N-(2-methylbutan-2-yl)-pyridine-4-carboxamide (0.78 g, 2.23 mmol) and commercially available (4-fluorophenyl)-boronic acid (312 mg, 2.23 mmol).

Example 1

N-tert-Butyl-2-(4-chlorophenyl)-6-(4-propan-2-yl-pyrimidin-5-yl)-pyridine-4-carboxamide

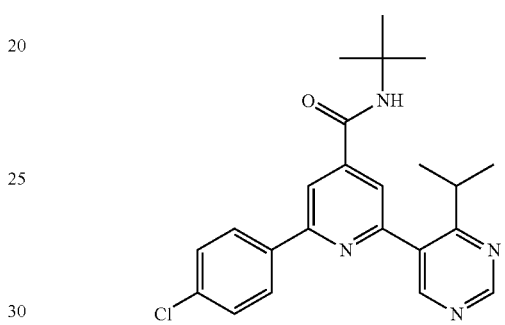

In a tube a mixture of 2-bromo-N-tert-butyl-6-(4-chlorophenyl)-pyridine-4-carboxamide (intermediate 2) (91.9 mg, 0.25 mmol), (4-isopropyl-pyrimidin-5-yl)-boronic acid (53.9 mg, 325 mol), 1,2-dimethoxyethane (1.7 ml) and 2M sodium carbonate solution (416 µl, 833 µmol) was purged with argon in an ultrasonic bath during 5 min, triphenylphosphine (13.1 mg, 50 µmol) and palladium(II)acetate (5.61 mg, 25 µmol) were added, the tube was sealed and the reaction mixture was allowed to stir for 5 h at 105° C. The crude reaction mixture was purified by flash chromatography on silica gel [heptane/ethyl acetate (20-80%)] to yield the title compound (69 mg, 68%) as a white foam, MS (ISP) m/z=409.2 [(M+H)⁺].

Example 2

N-tert-Butyl-2-(4-fluorophenyl)-6-(4-propan-2-yl-pyrimidin-5-yl)-pyridine-4-carboxamide

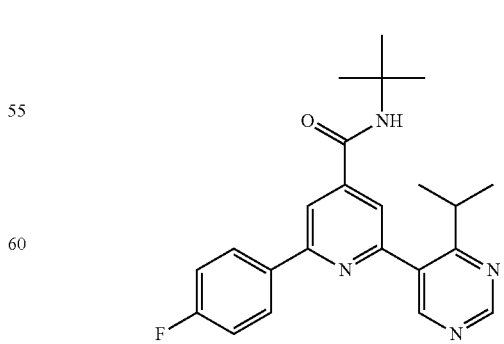

The title compound, light brown foam (69 mg, 70%), MS (ISP) m/z=393.3 [(M+H)⁺], was prepared in accordance with the general method of example 1 from 2-bromo-N-tertbutyl-6-(4-fluorophenyl)-pyridine-4-carboxamide (intermediate 1) (87.8 mg, 0.25 mmol) and commercially available (4-isopropyl-pyrimidin-5-yl)-boronic acid (53.9 mg, 325 µmol).

Example 3

N-tert-Butyl-2-(4-propan-2-yl-pyrimidin-5-yl)-6-[4-(trifluoromethyl)-phenyl]-pyridine-4-carboxamide

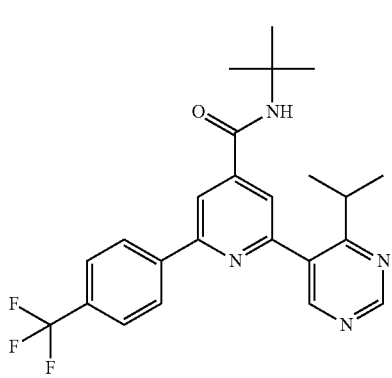 [SMILES: CC(C)c1ncncc1-c1cc(C(=O)NC(C)(C)C)cc(-c2ccc(C(F)(F)F)cc2)n1]

The title compound, off-white foam (79 mg, 71%), MS (ISP) m/z=443.3 [(M+H)⁺], was prepared in accordance with the general method of example 1 from 2-bromo-N-tert-butyl-6-[4-(trifluoromethyl)-phenyl]-pyridine-4-carboxamide (intermediate 3) (100 mg, 0.25 mmol) and commercially available (4-isopropyl-pyrimidin-5-yl)-boronic acid (53.9 mg, 325 µmol).

Example 4

N-tert-Butyl-2-(4-fluorophenyl)-6-(4-methylpyridin-3-yl)-pyridine-4-carboxamide

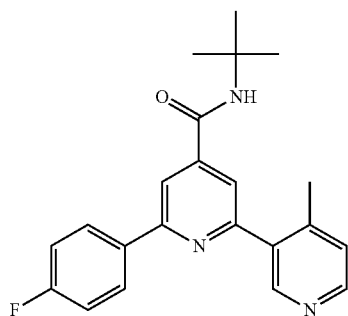 [SMILES: Cc1ccncc1-c1cc(C(=O)NC(C)(C)C)cc(-c2ccc(F)cc2)n1]

The title compound, light yellow foam (40 mg, 44%), MS (ISP) m/z=364.2 [(M+H)⁺], was prepared in accordance with the general method of example 1 from 2-bromo-N-tert-butyl-6-(4-fluorophenyl)-pyridine-4-carboxamide (intermediate 1) (87.8 mg, 0.25 mmol) and commercially available (4-methylpyridin-3-yl)-boronic acid (44.5 mg, 325 µmol).

Example 5

N-tert-Butyl-2-(4-chlorophenyl)-6-(4-methylpyridin-3-yl)-pyridine-4-carboxamide

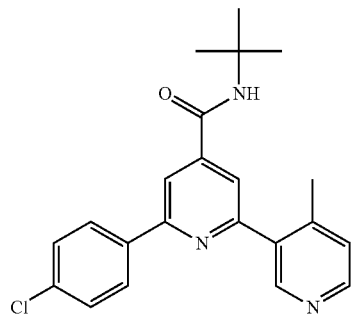 [SMILES: Cc1ccncc1-c1cc(C(=O)NC(C)(C)C)cc(-c2ccc(Cl)cc2)n1]

The title compound, off-white foam (31 mg, 33%), MS (ISP) m/z=380.2 [(M+H)⁺], was prepared in accordance with the general method of example 1 from 2-bromo-N-tert-butyl-6-(4-chlorophenyl)-pyridine-4-carboxamide (intermediate 2) (91.9 mg, 0.25 mmol) and commercially available (4-methylpyridin-3-yl)-boronic acid (44.5 mg, 325 µmol).

Example 6

N-tert-Butyl-2-(4-methylphenyl)-6-(4-propan-2-yl-pyrimidin-5-yl)-pyridine-4-carboxamide

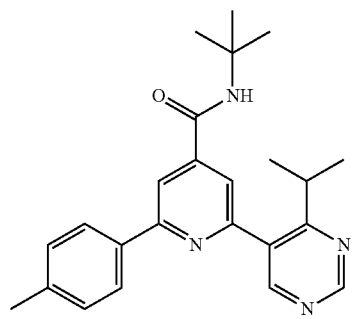 [SMILES: Cc1ccc(-c2cc(C(=O)NC(C)(C)C)cc(-c3cncnc3C(C)C)n2)cc1]

The title compound, off-white foam (70 mg, 72%), MS (ISP) m/z=389.2 [(M+H)⁺], was prepared in accordance with the general method of example 1 from 2-bromo-N-tert-butyl-6-(4-propan-2-yl-pyrimidin-5-yl)-pyridine-4-carboxamide (intermediate 4) (94.3 mg, 0.25 mmol) and commercially available p-tolylboronic acid (44.2 mg, 325 µmol).

Example 7

N-tert-Butyl-2-(3,4-difluorophenyl)-6-(4-propan-2-yl-pyrimidin-5-yl)-pyridine-4-carboxamide

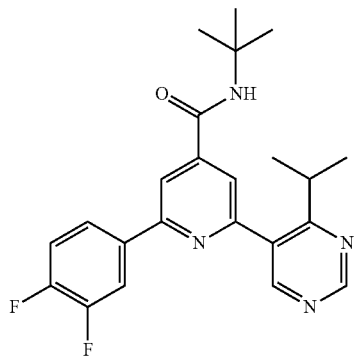 [SMILES: CC(C)c1ncncc1-c1cc(C(=O)NC(C)(C)C)cc(-c2ccc(F)c(F)c2)n1]

The title compound, light yellow solid (90 mg, 88%), MS (ISP) m/z=411.2 [(M+H)$^+$], mp 178° C., was prepared in accordance with the general method of example 1 from 2-bromo-N-tert-butyl-6-(4-propan-2-yl-pyrimidin-5-yl)-pyridine-4-carboxamide (intermediate 4) (94.3 mg, 0.25 mmol) and commercially available (3,4-difluoro-phenyl)-boronic acid (51.3 mg, 325 µmol).

Example 8

N-tert-Butyl-2-(4-fluoro-3-methylphenyl)-6-(4-propan-2-yl-pyrimidin-5-yl)-pyridine-4-carboxamide

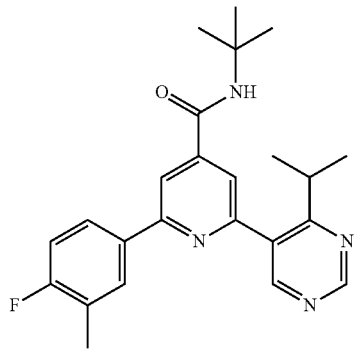 [SMILES: Cc1cc(-c2cc(C(=O)NC(C)(C)C)cc(-c3cncnc3C(C)C)n2)ccc1F]

The title compound, light yellow foam (93 mg, 92%), MS (ISP) m/z=407.2 [(M+H)$^+$], was prepared in accordance with the general method of example 1 from 2-bromo-N-tert-butyl-6-(4-propan-2-yl-pyrimidin-5-yl)-pyridine-4-carboxamide (intermediate 4) (94.3 mg, 0.25 mmol) and commercially available (4-fluoro-3-methyl-phenyl)boronic acid (50.0 mg, 325 µmol).

Example 9

N-tert-Butyl-2-(4-chloro-3-fluorophenyl)-6-(4-propan-2-yl-pyrimidin-5-yl)-pyridine-4-carboxamide

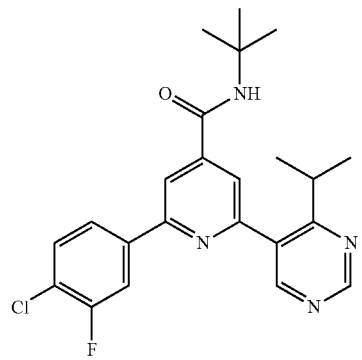

The title compound, white foam (52 mg, 49%), MS (ISP) m/z=427.2 [(M+H)$^+$], was prepared in accordance with the general method of example 1 from 2-bromo-N-tert-butyl-6-(4-propan-2-yl-pyrimidin-5-yl)-pyridine-4-carboxamide (intermediate 4) (94.3 mg, 0.25 mmol) and commercially available 4-chloro-3-fluoro-phenylboronic acid (56.7 mg, 325 µmol).

Example 10

N-tert-Butyl-2-(4-cyclopropyl-phenyl)-6-(4-propan-2-yl-pyrimidin-5-yl)-pyridine-4-carboxamide

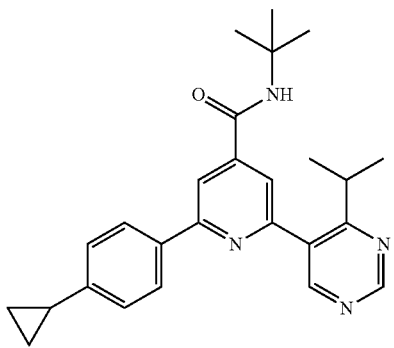 [SMILES: CC(C)c1ncncc1-c1cc(C(=O)NC(C)(C)C)cc(-c2ccc(C3CC3)cc2)n1]

The title compound, light yellow foam (96 mg, 93%), MS (ISP) m/z=415.3 [(M+H)$^+$], was prepared in accordance with the general method of example 1 from 2-bromo-N-tert-butyl-6-(4-propan-2-yl-pyrimidin-5-yl)-pyridine-4-carboxamide (intermediate 4) (94.3 mg, 0.25 mmol) and commercially available (4-cyclopropyl-phenyl)-boronic acid (52.6 mg, 325 µmol).

Example 11

2-(4-Chlorophenyl)-N-(2-cyclopropyl-propan-2-yl)-6-(4-propan-2-yl-pyrimidin-5-yl)-pyridine-4-carboxamide

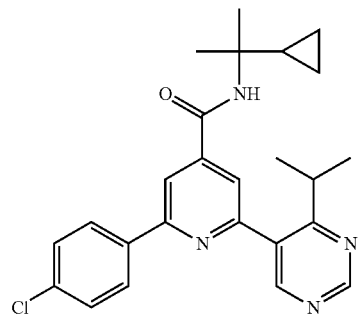 [SMILES: CC(C)c1ncncc1-c1cc(C(=O)NC(C)(C)C2CC2)cc(-c2ccc(Cl)cc2)n1]

The title compound, off-white foam (92 mg, 85%), MS (ISP) m/z=435.2 [(M+H)$^+$], was prepared in accordance with the general method of example 1 from 2-bromo-6-(4-chlorophenyl)-N-(2-cyclopropylpropan-2-yl)-pyridine-4-carboxamide (intermediate 5) (98.4 mg, 0.25 mmol) and commercially available (4-isopropyl-pyrimidin-5-yl)-boronic acid (53.9 mg, 325 mol).

Example 12

2-(4-Chlorophenyl)-N-(2-cyanopropan-2-yl)-6-(4-propan-2-yl-pyrimidin-5-yl)-pyridine-4-carboxamide

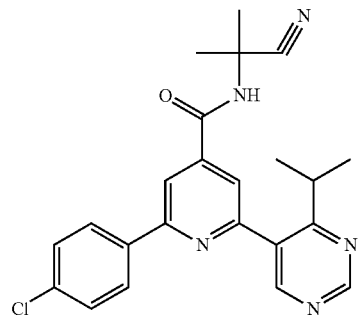 [SMILES: CC(C)c1ncncc1-c1cc(C(=O)NC(C)(C)C#N)cc(-c2ccc(Cl)cc2)n1]

The title compound, off-white foam (48 mg, 46%), MS (ISP) m/z=420.2 [(M+H)$^+$], was prepared in accordance with the general method of example 1 from 2-bromo-6-(4-chlorophenyl)-N-(2-cyanopropan-2-yl)-pyridine-4-carboxamide (intermediate 7) (94.7 mg, 0.25 mmol) and commercially available (4-isopropyl-pyrimidin-5-yl)-boronic acid (53.9 mg, 325 mol).

Example 13

2-(4-Chlorophenyl)-N-(1-hydroxy-2-methylpropan-2-yl)-6-(4-propan-2-yl-pyrimidin-5-yl)-pyridine-4-carboxamide

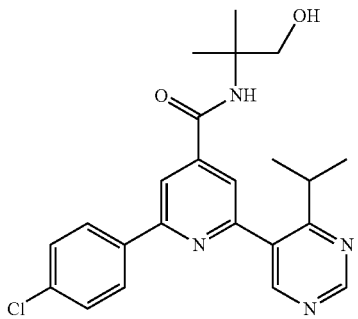 [SMILES: CC(C)c1ncncc1-c1cc(C(=O)NC(C)(C)CO)cc(-c2ccc(Cl)cc2)n1]

The title compound, white foam (67 mg, 63%), MS (ISP) m/z=425.2 [(M+H)$^+$], was prepared in accordance with the general method of example 1 from 2-bromo-6-(4-chlorophenyl)-N-(1-hydroxy-2-methylpropan-2-yl)-pyridine-4-carboxamide (intermediate 8) (95.9 mg, 0.25 mmol) and commercially available (4-isopropyl-pyrimidin-5-yl)-boronic acid (53.9 mg, 325 μmol).

Example 14

2-(4-Chlorophenyl)-6-(4-propan-2-yl-pyrimidin-5-yl)-N-(1,1,1-trifluoro-2-methylpropan-2-yl)-pyridine-4-carboxamide

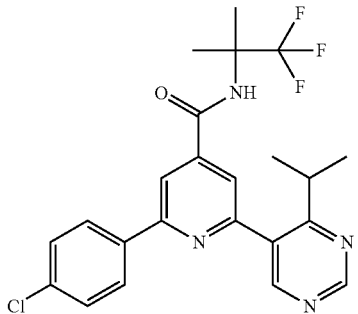 [SMILES: CC(C)c1ncncc1-c1cc(C(=O)NC(C)(C)C(F)(F)F)cc(-c2ccc(Cl)cc2)n1]

The title compound, light yellow foam (73 mg, 63%), MS (ISP) m/z=463.2 [(M+H)$^+$], was prepared in accordance with the general method of example 1 from 2-bromo-6-(4-chlorophenyl)-N-(1,1,1-trifluoro-2-methylpropan-2-yl)-pyridine-4-carboxamide (intermediate 6) (105 mg, 0.25 mmol) and commercially available (4-isopropyl-pyrimidin-5-yl)-boronic acid (53.9 mg, 325 μmol).

Example 15

N-tert-Butyl-2-(4-methoxyphenyl)-6-(4-propan-2-yl-pyrimidin-5-yl)-pyridine-4-carboxamide

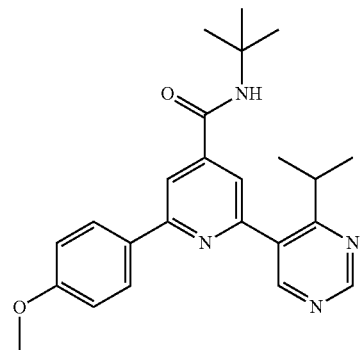 [SMILES: COc1ccc(-c2cc(C(=O)NC(C)(C)C)cc(-c3cncnc3C(C)C)n2)cc1]

The title compound, off-white foam (98 mg, 97%), MS (ISP) m/z=405.2 [(M+H)+], was prepared in accordance with the general method of example 1 from 2-bromo-N-tert-butyl-6-(4-propan-2-yl-pyrimidin-5-yl)-pyridine-4-carboxamide (intermediate 4) (94.3 mg, 0.25 mmol) and commercially available (4-methoxyphenyl)-boronic acid (49.4 mg, 325 µmol).

Example 16

N-tert-Butyl-2-(3-fluoro-4-methylphenyl)-6-(4-propan-2-yl-pyrimidin-5-yl)-pyridine-4-carboxamide

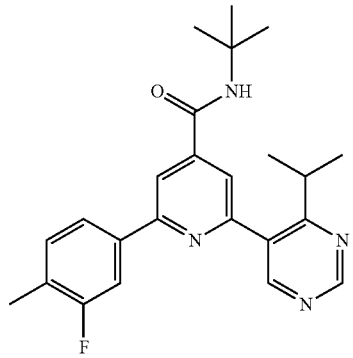 [SMILES: Cc1ccc(-c2cc(C(=O)NC(C)(C)C)cc(-c3cncnc3C(C)C)n2)cc1F]

The title compound, light brown foam (67 mg, 84%), MS (ISP) m/z=407.2 [(M+H)+], was prepared in accordance with the general method of example 1 from 2-bromo-N-tert-butyl-6-(4-propan-2-yl-pyrimidin-5-yl)-pyridine-4-carboxamide (intermediate 4) (74.0 mg, 196 µmol) and commercially available 3-fluoro-4-methyl-phenylboronic acid (39.3 mg, 255 µmol).

Example 17

(RS)-2-(4-Fluorophenyl)-N-(3-methyl-1,1-dioxothiolan-3-yl)-6-(4-propan-2-yl-pyrimidin-5-yl)-pyridine-4-carboxamide

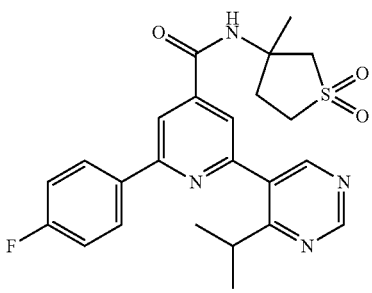 [SMILES: CC(C)c1ncncc1-c1cc(C(=O)NC2(C)CCS(=O)(=O)C2)cc(-c2ccc(F)cc2)n1]

The title compound, light yellow foam (104 mg, 89%), MS (ISP) m/z=469.3 [(M+H)+], was prepared in accordance with the general method of example 1 from (RS)-2-bromo-6-(4-fluorophenyl)-N-(3-methyl-1,1-dioxothiolan-3-yl)-pyridine-4-carboxamide (intermediate 9) (107 mg, 0.25 mmol) and commercially available (4-isopropyl-pyrimidin-5-yl)-boronic acid (49.8 mg, 300 µmol).

Example 18

2-(4-Fluorophenyl)-N-(2-methylbutan-2-yl)-6-(4-propan-2-yl-pyrimidin-5-yl)-pyridine-4-carboxamide

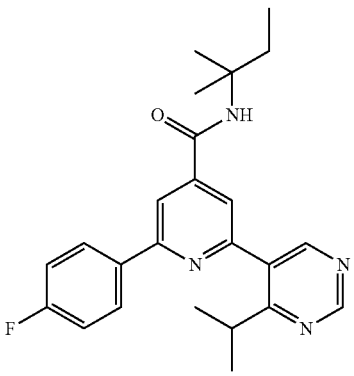 [SMILES: CCC(C)(C)NC(=O)c1cc(-c2ccc(F)cc2)nc(-c2cncnc2C(C)C)c1]

The title compound, light yellow foam (89 mg, 88%), MS (ISP) m/z=407.3 [(M+H)+], was prepared in accordance with the general method of example 1 from 2-bromo-6-(4-fluorophenyl)-N-(2-methylbutan-2-yl)-pyridine-4-carboxamide (intermediate 10) (91.3 mg, 0.25 mmol) and commercially available (4-isopropyl-pyrimidin-5-yl)-boronic acid (49.8 mg, 300 µmol).

Example 19

N-tert-Butyl-2-(4-ethyl-pyrimidin-5-yl)-6-(4-fluoro-phenyl)-pyridine-4-carboxamide

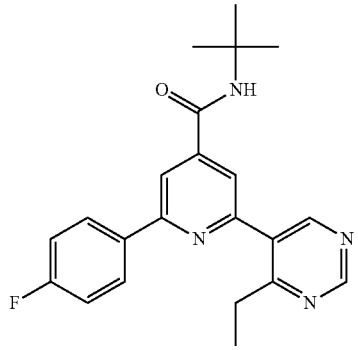 [SMILES: CCc1ncncc1-c1cc(C(=O)NC(C)(C)C)cc(-c2ccc(F)cc2)n1]

The title compound, colorless semisolid (33 mg, 35%), MS (ISP) m/z=379.3 [(M+H)+], was prepared in accordance with the general method of example 1 from 2-bromo-N-tert-butyl-6-(4-fluorophenyl)-pyridine-4-carboxamide (intermediate 1) (87.8 mg, 0.25 mmol) and commercially available 4-ethyl-5-(4,4,5,5-tetramethyl-1,3,2-dioxaborolan-2-yl)-pyrimidine [CAS-No. 1375303-42-6] (76.1 mg, 325 μmol).

Example 20

N-tert-Butyl-2-(4-fluorophenyl)-6-(4-methylpyrimidin-5-yl)-pyridine-4-carboxamide

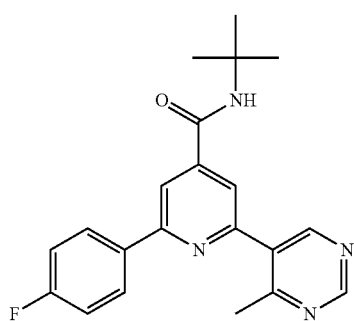 [SMILES: Cc1ncncc1-c1cc(C(=O)NC(C)(C)C)cc(-c2ccc(F)cc2)n1]

The title compound, off-white foam (21 mg, 22%), MS (ISP) m/z=365.3 [(M+H)+], was prepared in accordance with the general method of example 1 from 2-bromo-N-tert-butyl-6-(4-fluorophenyl)-pyridine-4-carboxamide (intermediate 1) (87.8 mg, 0.25 mmol) and commercially available 4-methyl-5-(4,4,5,5-tetramethyl-1,3,2-dioxaborolan-2-yl)-pyrimidine [CAS-No. 1370001-96-9] (82.5 mg, 375 μmol).

Example 21

N-tert-Butyl-2-(4-cyclopropylpyrimidin-5-yl)-6-(4-fluorophenyl)-pyridine-4-carboxamide

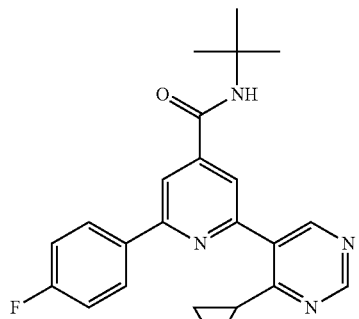

The title compound, off-white foam (9 mg, 9%), MS (ISP) m/z=391.3 [(M+H)+], was prepared in accordance with the general method of example 1 from 2-bromo-N-tert-butyl-6-(4-fluorophenyl)-pyridine-4-carboxamide (intermediate 1) (87.8 mg, 0.25 mmol) and commercially available 4-cyclopropyl-5-(4,4,5,5-tetramethyl-1,3,2-dioxaborolan-2-yl)-pyrimidine [CAS-No. 1375303-49-3] (92.3 mg, 375 μmol).

Example 22

N-tert-Butyl-2-(4-tert-butyl-pyrimidin-5-yl)-6-(4-fluorophenyl)-pyridine-4-carboxamide

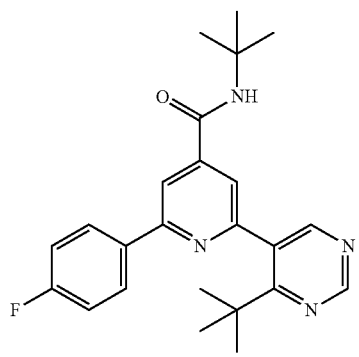 [SMILES: CC(C)(C)NC(=O)c1cc(-c2ccc(F)cc2)nc(-c2cncnc2C(C)(C)C)c1]

Step A

To a stirred solution of commercially available 5-bromo-4-(tert-butyl)-pyrimidine (215 mg, 1 mmol) in THF (1 ml) and toluene (4 ml) was added triisopropyl borate (229 mg, 282 μl, 1.22 mmol) at −78° C. followed by a drop-wise addition of n-butyl lithium (1.6N in hexane) (731 μl, 1.17 mmol) at −78° C. The solution was allowed to stir at −78° C. for 45 min and then allowed to warm to room temperature. The reaction mixture was quenched by addition of 1M hydrochloride solution (2.5 ml) to pH=1, diluted with water (5 ml) and extracted with diethyl acetate (2×40 ml). The combined organic layers were washed with brine (30 ml), dried (MgSO4) and evaporated to yield (4-(tert-butyl)-pyrimidin-5-yl)-boronic acid (135 mg) as a light yellow oil, MS (ISP) m/z=181.1 [(M+H)+], which was used without further purification.

Step B

The title compound, off-white foam (95 mg, 94%), MS (ISP) m/z=349.2 [(M+H)⁺], was prepared in accordance with the general method of example 1 from 2-bromo-N-tert-butyl-6-(4-fluorophenyl)-pyridine-4-carboxamide (intermediate 1) (87.8 mg, 0.25 mmol) and (4-(tert-butyl)-pyrimidin-5-yl)-boronic acid (65.0 mg, 0.36 mmol).

Example 23

N-tert-Butyl-2-(4-tert-butylpyrimidin-5-yl)-6-(4-chlorophenyl)-pyridine-4-carboxamide

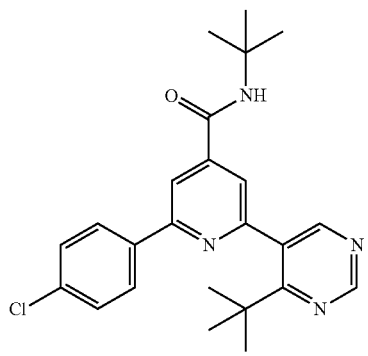 [SMILES: CC(C)(C)NC(=O)c1cc(-c2ccc(Cl)cc2)nc(-c2cncnc2C(C)(C)C)c1]

The title compound, off-white foam (69 mg, 65%), MS (ISP) m/z=423.3 [(M+H)⁺], was prepared in accordance with the general method of example 1 from 2-bromo-N-tert-butyl-6-(4-chlorophenyl)-pyridine-4-carboxamide (intermediate 2) (91.9 mg, 0.25 mmol) and (4-(tert-butyl)-pyrimidin-5-yl)-boronic acid (example 22, step A) (65.0 mg, 0.36 mmol).

Example 24

N-tert-Butyl-2-(4-tert-butyl-pyrimidin-5-yl)-6-[4-(trifluoromethyl)-phenyl]-pyridine-4-carboxamide

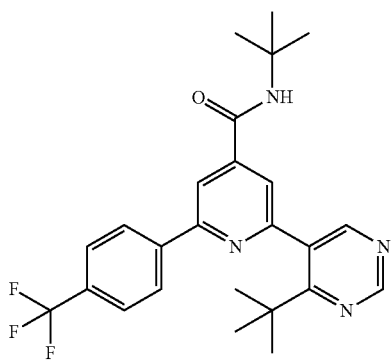 [SMILES: CC(C)(C)NC(=O)c1cc(-c2ccc(C(F)(F)F)cc2)nc(-c2cncnc2C(C)(C)C)c1]

The title compound, light yellow foam (76 mg, 67%), MS (ISP) m/z=457.3 [(M+H)⁺], was prepared in accordance with the general method of example 1 from 2-bromo-N-tert-butyl-6-[4-(trifluoromethyl)-phenyl]-pyridine-4-carboxamide (intermediate 3) (100 mg, 0.25 mmol) and (4-(tert-butyl)-pyrimidin-5-yl)-boronic acid (example 22, step A) (65.0 mg, 0.36 mmol).

Example 25

N-tert-Butyl-2-(4-propan-2-yl-pyridin-3-yl)-6-[4-(trifluoromethyl)-phenyl]-pyridine-4-carboxamide

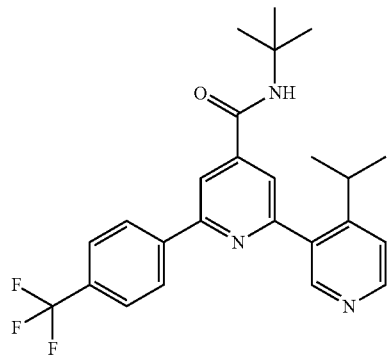 [SMILES: CC(C)c1ccncc1-c1cc(C(=O)NC(C)(C)C)cc(-c2ccc(C(F)(F)F)cc2)n1]

The title compound, white foam (110 mg, 100%), MS (ISP) m/z=442.3 [(M+H)⁺], was prepared in accordance with the general method of example 1 from 2-bromo-N-tert-butyl-6-[4-(trifluoromethyl)-phenyl]-pyridine-4-carboxamide (intermediate 3) (100 mg, 0.25 mmol) and commercially available (4-isopropyl-pyridin-3-yl)-boronic acid (53.6 mg, 325 µmol).

Example 26

N-tert-Butyl-2-(4-chlorophenyl)-6-(4-propan-2-yl-pyridin-3-yl)-pyridine-4-carboxamide

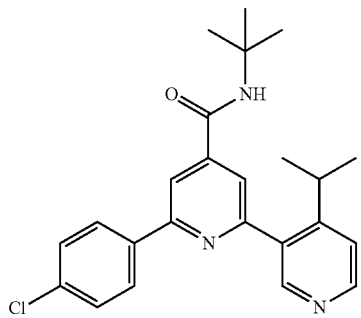 [SMILES: CC(C)c1ccncc1-c1cc(C(=O)NC(C)(C)C)cc(-c2ccc(Cl)cc2)n1]

The title compound, white foam (102 mg, 100%), MS (ISP) m/z=408.2 [(M+H)⁺], was prepared in accordance with the general method of example 1 from 2-bromo-N-tert-butyl-6-(4-chlorophenyl)-pyridine-4-carboxamide (intermediate 2) (91.9 mg, 0.25 mmol) and commercially available (4-isopropyl-pyridin-3-yl)-boronic acid (53.6 mg, 325 µmol).

Example 27

N-tert-Butyl-2-(4-fluorophenyl)-6-(4-propan-2-yl-pyridin-3-yl)-pyridine-4-carboxamide

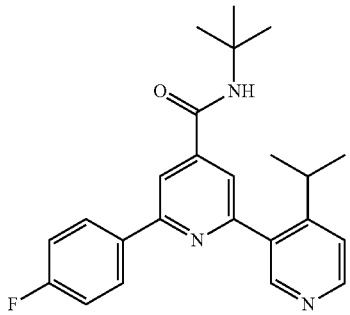 [SMILES: CC(C)c1ccncc1-c1cc(C(=O)NC(C)(C)C)cc(-c2ccc(F)cc2)n1]

The title compound, white foam (97 mg, 99%), MS (ISP) m/z=392.2 [(M+H)$^+$], was prepared in accordance with the general method of example 1 from 2-bromo-N-tert-butyl-6-(4-fluorophenyl)-pyridine-4-carboxamide (intermediate 1) (87.8 mg, 0.25 mmol) and commercially available (4-isopropyl-pyridin-3-yl)-boronic acid (53.6 mg, 325 µmol).

The invention claimed is:
1. A compound of formula I:

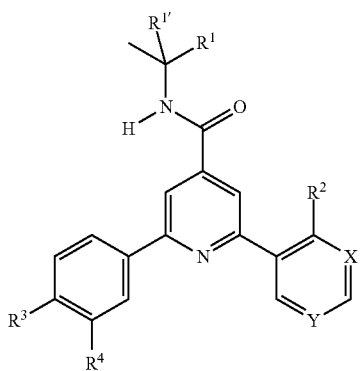

wherein
R$^{1'}$ is methyl;
R$^1$ is methyl, ethyl, CF$_3$, CH$_2$OH, cyclopropyl or cyano, or R$^{1'}$ and R$^1$ may form together a 1,1-dioxo-tetrahydro-thiophen-3-yl ring;
R$^2$ is hydrogen, methyl, ethyl, isopropyl, tert-butyl, cyclopropyl, cyclopropylmethyl, or hydroxmethyl;
R$^3$ is Cl, F, CF$_3$, methyl, methoxy, or cyclopropyl;
R$^4$ is hydrogen, methyl, F or Cl;
X is N or CH;
Y is N or CH;
  with the proviso that X and Y are not simultaneously CH;
or a pharmaceutically acceptable salt or acid addition salt, a racemic mixture, or its corresponding enantiomer and/or optical isomer and/or stereoisomer.

2. A compound of formula IA according to claim 1:

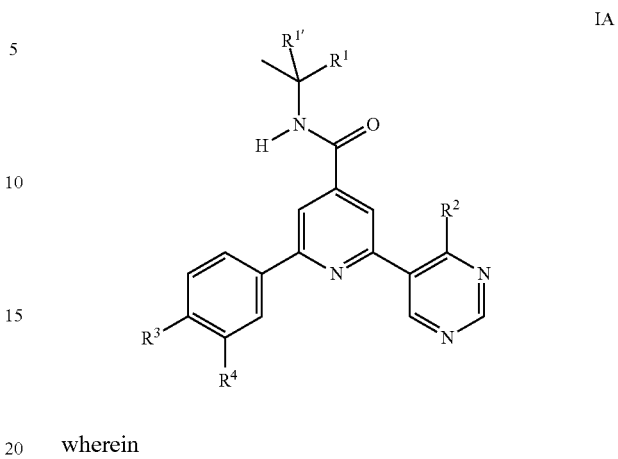

wherein
R$^{1''}$ is methyl;
R$^1$ is methyl, ethyl, CF$_3$, CH$_2$OH, cyclopropyl or cyano, or R$^{1'}$ and R$^1$ may form together a 1,1-dioxo-tetrahydro-thiophen-3-yl ring;
R$^2$ is hydrogen, methyl, ethyl, isopropyl, tert-butyl, cyclopropyl, cyclopropylmethyl, or hydroxmethyl;
R$^3$ is Cl, F, CF$_3$, methyl, methoxy, or cyclopropyl;
R$^4$ is hydrogen, methyl, F or Cl;
or a pharmaceutically acceptable salt or acid addition salt, a racemic mixture, or its corresponding enantiomer and/or optical isomer and/or stereoisomer.

3. A compound of formula IA according to claim 2, or a pharmaceutically acceptable salt thereof, wherein the compound is selected from the group consisting of
N-tert-Butyl-2-(4-chlorophenyl)-6-(4-propan-2-yl-pyrimidin-5-yl)-pyridine-4-carboxamide;
N-tert-Butyl-2-(4-fluorophenyl)-6-(4-propan-2-yl-pyrimidin-5-yl)-pyridine-4-carboxamide;
N-tert-Butyl-2-(4-propan-2-yl-pyrimidin-5-yl)-6-[4-(trifluoromethyl)-phenyl]-pyridine-4-carboxamide;
N-tert-Butyl-2-(4-methylphenyl)-6-(4-propan-2-yl-pyrimidin-5-yl)-pyridine-4-carboxamide;
N-tert-Butyl-2-(3,4-difluorophenyl)-6-(4-propan-2-yl-pyrimidin-5-yl)-pyridine-4-carboxamide;
N-tert-Butyl-2-(4-fluoro-3-methylphenyl)-6-(4-propan-2-yl-pyrimidin-5-yl)-pyridine-4-carboxamide;
N-tert-Butyl-2-(4-chloro-3-fluorophenyl)-6-(4-propan-2-yl-pyrimidin-5-yl)-pyridine-4-carboxamide;
N-tert-Butyl-2-(4-cyclopropyl-phenyl)-6-(4-propan-2-yl-pyrimidin-5-yl)-pyridine-4-carboxamide;
2-(4-Chlorophenyl)-N-(2-cyclopropyl-propan-2-yl)-6-(4-propan-2-yl-pyrimidin-5-yl)-pyridine-4-carboxamide;
2-(4-Chlorophenyl)-N-(2-cyanopropan-2-yl)-6-(4-propan-2-yl-pyrimidin-5-yl)-pyridine-4-carboxamide;
2-(4-Chlorophenyl)-N-(1-hydroxy-2-methylpropan-2-yl)-6-(4-propan-2-yl-pyrimidin-5-yl)-pyridine-4-carboxamide;
2-(4-Chlorophenyl)-6-(4-propan-2-yl-pyrimidin-5-yl)-N-(1,1,1-trifluoro-2-methylpropan-2-yl)-pyridine-4-carboxamide;
N-tert-Butyl-2-(4-methoxyphenyl)-6-(4-propan-2-yl-pyrimidin-5-yl)-pyridine-4-carboxamide;
N-tert-Butyl-2-(3-fluoro-4-methylphenyl)-6-(4-propan-2-yl-pyrimidin-5-yl)-pyridine-4-carboxamide;
(RS)-2-(4-Fluorophenyl)-N-(3-methyl-1,1-dioxothiolan-3-yl)-6-(4-propan-2-yl-pyrimidin-5-yl)-pyridine-4-carboxamide;
2-(4-Fluorophenyl)-N-(2-methylbutan-2-yl)-6-(4-propan-2-yl-pyrimidin-5-yl)-pyridine-4-carboxamide;

N-tert-Butyl-2-(4-ethyl-pyrimidin-5-yl)-6-(4-fluorophenyl)-pyridine-4-carboxamide;
N-tert-Butyl-2-(4-fluorophenyl)-6-(4-methylpyrimidin-5-yl)-pyridine-4-carboxamide;
N-tert-Butyl-2-(4-cyclopropylpyrimidin-5-yl)-6-(4-fluorophenyl)-pyridine-4-carboxamide;
N-tert-Butyl-2-(4-tert-butyl-pyrimidin-5-yl)-6-(4-fluorophenyl)-pyridine-4-carboxamide;
N-tert-Butyl-2-(4-tert-butylpyrimidin-5-yl)-6-(4-chlorophenyl)-pyridine-4-carboxamide; and
N-tert-Butyl-2-(4-tert-butyl-pyrimidin-5-yl)-6-[4-(trifluoromethyl)-phenyl]-pyridine-4-carboxamide.

4. A compound of formula IB according to claim 1:

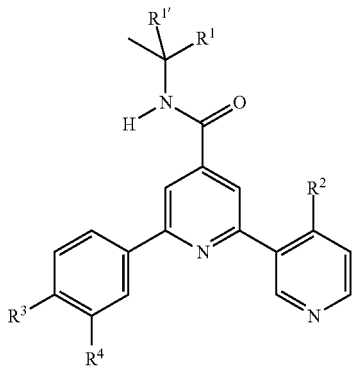

IB wherein
$R^{1'}$ is methyl;
$R^1$ is methyl, ethyl, $CF_3$, $CH_2OH$, cyclopropyl or cyano, or $R^{1'}$ and $R^1$ may form together a 1,1-dioxo-tetrahydro-thiophen-3-yl ring;
$R^2$ is hydrogen, methyl, ethyl, isopropyl, tert-butyl, cyclopropyl, cyclopropylmethyl, or hydroxmethyl;
$R^3$ is Cl, F, $CF_3$, methyl, methoxy, or cyclopropyl;
$R^4$ is hydrogen, methyl, F or Cl;
or a pharmaceutically acceptable salt or acid addition salt, a racemic mixture, or its corresponding enantiomer and/or optical isomer and/or stereoisomer.

5. A compound of formula IB according to claim 4, or a pharmaceutically acceptable salt thereof, wherein the compound is selected from the group consisting of
N-tert-Butyl-2-(4-fluorophenyl)-6-(4-methylpyridin-3-yl)-pyridine-4-carboxamide;
N-tert-Butyl-2-(4-chlorophenyl)-6-(4-methylpyridin-3-yl)-pyridine-4-carboxamide;
N-tert-Butyl-2-(4-propan-2-yl-pyridin-3-yl)-6-[4-(trifluoromethyl)-phenyl]-pyridine-4-carboxamide;
N-tert-Butyl-2-(4-chlorophenyl)-6-(4-propan-2-yl-pyridin-3-yl)-pyridine-4-carboxamide; and
N-tert-Butyl-2-(4-fluorophenyl)-6-(4-propan-2-yl-pyridin-3-yl)-pyridine-4-carboxamide.

6. A process for the manufacture of a compound of formula I, or a pharmaceutically acceptable salt thereof, as defined in claim 1, which process comprises:
a) reacting a compound of formula

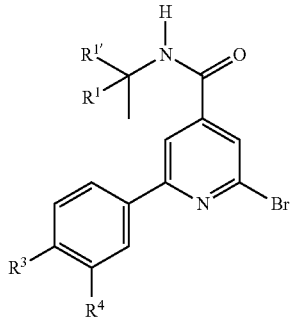

II with a compound of formula

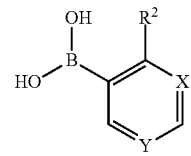

III to form a compound of formula I

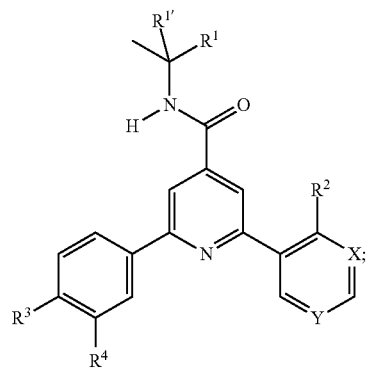

I or
b) reacting a compound of formula

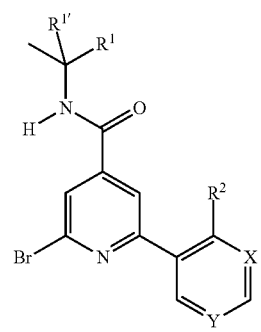

IV with a compound of formula

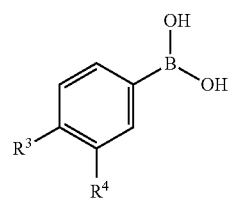

V to form a compound of formula I

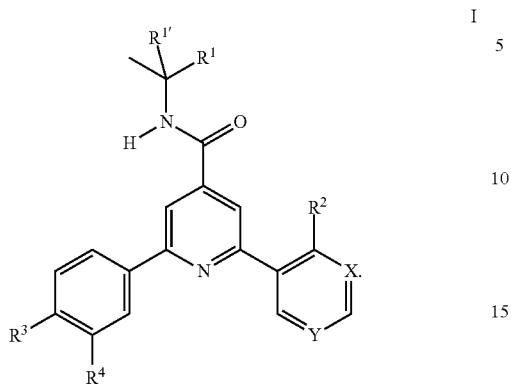

7. A pharmaceutical composition comprising a compound of formula I as claimed in claim 1, or a pharmaceutically acceptable salt thereof, and one or more pharmaceutically acceptable excipients.

8. A method for the treatment of schizophrenia, bipolar disorder, obsessive-compulsive disorder or autism spectrum disorder in a mammal, which method comprises administering an effective amount of a compound of formula I as claimed in claim 1, or a pharmaceutically acceptable salt thereof, to the mammal.

\* \* \* \* \*